(12) United States Patent
Hartwell et al.

(10) Patent No.: US 11,357,906 B2
(45) Date of Patent: Jun. 14, 2022

(54) SYSTEMS AND METHODS FOR DETECTING OPERATIONAL CONDITIONS OF REDUCED PRESSURE THERAPY

(71) Applicant: Smith & Nephew, Inc., Memphis (GB)

(72) Inventors: Edward Yerbury Hartwell, Hull (GB); Felix C. Quintanar, Hull (GB); Jason Peter De Villiers, Cambridge (GB)

(73) Assignee: Smith & Nephew, Inc., Memphis, TN (US)

(*) Notice: Subject to any disclaimer, the term of this patent is extended or adjusted under 35 U.S.C. 154(b) by 689 days.

(21) Appl. No.: 16/077,429

(22) PCT Filed: Feb. 10, 2017

(86) PCT No.: PCT/US2017/017538
§ 371 (c)(1),
(2) Date: Aug. 10, 2018

(87) PCT Pub. No.: WO2017/139686
PCT Pub. Date: Aug. 17, 2017

(65) Prior Publication Data
US 2020/0376175 A1    Dec. 3, 2020

Related U.S. Application Data

(60) Provisional application No. 62/294,725, filed on Feb. 12, 2016, provisional application No. 62/294,816, (Continued)

(51) Int. Cl.
*A61M 1/00* (2006.01)
(52) U.S. Cl.
CPC ............ *A61M 1/962* (2021.05); *A61M 1/732* (2021.05); *A61M 1/734* (2021.05);
(Continued)

(58) Field of Classification Search
CPC ........ A61M 1/90; A61M 1/962; A61M 1/966; A61M 1/71; A61M 1/73; A61M 1/95;
(Continued)

(56) References Cited

U.S. PATENT DOCUMENTS 4,832,299 A    5/1989    Gorton et al.
5,219,428 A    6/1993    Stern
(Continued)

FOREIGN PATENT DOCUMENTS

DE    102010036405 A1    1/2012
GB    2235877 A    3/1991
(Continued)

OTHER PUBLICATIONS

Hartmann Vivano., "Vivano—Product Application Description," retrieved from http://www.vivanosystem.info/20809.php, accessed on Feb. 28, 2013, 3 pages.
(Continued)

*Primary Examiner* — Andrew J Mensh
(74) *Attorney, Agent, or Firm* — Knobbe, Martens, Olson & Bear, LLP

(57) ABSTRACT

In some embodiments, a negative pressure wound therapy system can detect and classify one or more operational conditions, including detection of a wound bleeding. The system can react to detection of blood by providing an indication, reducing the intensity or stopping therapy, releasing negative pressure, etc. In certain embodiments, the system can detect one or more additional operational conditions, such as change in vacuum pressure, gas leak rate change, exudate flow rate change, water flow rate change, presence of exudate, presence of water, etc. The system can detect and distinguish between different operational conditions and provide indication or take remedial action.

19 Claims, 19 Drawing Sheets

Related U.S. Application Data filed on Feb. 12, 2016, provisional application No. 62/305,475, filed on Mar. 8, 2016.

(52) U.S. Cl.
CPC . *A61M 2205/18* (2013.01); *A61M 2205/3334* (2013.01); *A61M 2205/50* (2013.01)

(58) Field of Classification Search
CPC .......... A61M 1/982; A61M 2205/3306; A61M 2205/3331; A61M 2205/3334; A61M 2205/3344; A61M 2205/3341; A61M 2205/50
USPC ........................................................ 604/543
See application file for complete search history.

(56) References Cited

U.S. PATENT DOCUMENTS

| | | | |
|---|---|---|---|
| 5,466,229 A | 11/1995 | Elson et al. | |
| 5,582,601 A | 12/1996 | Wortrich et al. | |
| 5,584,824 A | 12/1996 | Gillette et al. | |
| 5,656,027 A | 8/1997 | Ellingboe | |
| 5,669,892 A | 9/1997 | Keogh et al. | |
| 5,693,013 A | 12/1997 | Geuder | |
| 6,755,807 B2 | 6/2004 | Risk, Jr. et al. | |
| 6,979,324 B2 | 12/2005 | Bybordi et al. | |
| 7,004,915 B2 | 2/2006 | Boynton et al. | |
| 7,128,735 B2 | 10/2006 | Weston | |
| 7,553,306 B1 | 6/2009 | Hunt et al. | |
| 7,608,066 B2 | 10/2009 | Vogel | |
| 7,615,036 B2 | 11/2009 | Joshi et al. | |
| 7,670,323 B2 | 3/2010 | Hunt et al. | |
| 7,758,555 B2 | 7/2010 | Kelch et al. | |
| 7,846,141 B2 | 12/2010 | Weston | |
| 7,862,339 B2 | 1/2011 | Mulligan | |
| 8,048,046 B2 | 11/2011 | Hudspeth et al. | |
| 8,061,360 B2 | 11/2011 | Locke et al. | |
| 8,167,869 B2 | 5/2012 | Wudyka | |
| 8,202,262 B2 | 6/2012 | Lina et al. | |
| 8,257,328 B2 | 9/2012 | Augustine et al. | |
| 8,267,918 B2 | 9/2012 | Johnson et al. | |
| 8,294,586 B2 | 10/2012 | Pidgeon et al. | |
| 8,366,690 B2 | 2/2013 | Locke et al. | |
| 8,409,170 B2 | 4/2013 | Locke et al. | |
| 8,439,882 B2 | 5/2013 | Kelch | |
| 8,449,508 B2 | 5/2013 | Coulthard et al. | |
| 8,480,641 B2 | 7/2013 | Jacobs | |
| 8,494,349 B2 | 7/2013 | Gordon | |
| 8,540,688 B2 | 9/2013 | Eckstein et al. | |
| 8,617,129 B2 | 12/2013 | Hartwell | |
| 8,622,981 B2 | 1/2014 | Hartwell et al. | |
| 8,652,111 B2 | 2/2014 | Pratt et al. | |
| 8,657,806 B2 | 2/2014 | Eckstein et al. | |
| 8,668,677 B2 | 3/2014 | Eckstein et al. | |
| 8,771,259 B2 | 7/2014 | Karpowicz et al. | |
| 8,814,840 B2 | 8/2014 | Evans et al. | |
| 8,814,841 B2 | 8/2014 | Hartwell | |
| 8,814,842 B2 | 8/2014 | Coulthard et al. | |
| 8,827,983 B2 | 9/2014 | Braga et al. | |
| 8,843,327 B2 | 9/2014 | Vernon-Harcourt et al. | |
| 8,845,603 B2 | 9/2014 | Middleton et al. | |
| 8,858,517 B2 | 10/2014 | Pan et al. | |
| 8,974,429 B2 | 3/2015 | Gordon et al. | |
| 9,084,845 B2 | 7/2015 | Adie et al. | |
| 9,326,683 B2 | 5/2016 | Ganapathy et al. | |
| 9,393,354 B2 | 7/2016 | Freedman et al. | |
| 9,408,954 B2 | 8/2016 | Gordon et al. | |
| 9,636,440 B2 | 5/2017 | Weston et al. | |
| 10,207,031 B2 | 2/2019 | Toth | |
| 2002/0026160 A1 | 2/2002 | Takahashi et al. | |
| 2002/0198504 A1 | 12/2002 | Risk et al. | |
| 2003/0093041 A1 | 5/2003 | Risk, Jr. et al. | |
| 2003/0164600 A1 | 9/2003 | Dunn et al. | |
| 2004/0064132 A1 | 4/2004 | Boehringer et al. | |
| 2004/0102743 A1 | 5/2004 | Walker | |
| 2005/0124966 A1 | 6/2005 | Karpowicz et al. | |
| 2005/0187528 A1 | 8/2005 | Berg | |
| 2005/0209560 A1 | 9/2005 | Boukhny et al. | |
| 2006/0029675 A1 | 2/2006 | Ginther | |
| 2006/0144440 A1 | 7/2006 | Merkle | |
| 2006/0149171 A1 | 7/2006 | Vogel et al. | |
| 2007/0032741 A1 | 2/2007 | Hibner et al. | |
| 2007/0078444 A1 | 4/2007 | Larsson | |
| 2007/0118096 A1 | 5/2007 | Smith et al. | |
| 2007/0179460 A1 | 8/2007 | Adahan | |
| 2007/0180904 A1 | 8/2007 | Gao | |
| 2007/0219532 A1* | 9/2007 | Karpowicz ........... A61M 1/882 604/540 |
| 2007/0233022 A1 | 10/2007 | Henley et al. | |
| 2007/0260226 A1 | 11/2007 | Jaeb et al. | |
| 2008/0015526 A1 | 1/2008 | Reiner et al. | |
| 2008/0051708 A1 | 2/2008 | Kumar et al. | |
| 2008/0082040 A1 | 4/2008 | Kubler et al. | |
| 2008/0082077 A1 | 4/2008 | Williams | |
| 2008/0125697 A1 | 5/2008 | Gao | |
| 2008/0125698 A1 | 5/2008 | Gerg et al. | |
| 2008/0243096 A1 | 10/2008 | Svedman | |
| 2009/0005746 A1 | 1/2009 | Nielsen et al. | |
| 2009/0043268 A1 | 2/2009 | Eddy et al. | |
| 2009/0101219 A1 | 4/2009 | Martini et al. | |
| 2010/0022990 A1 | 1/2010 | Karpowicz et al. | |
| 2010/0036333 A1 | 2/2010 | Schenk, III et al. | |
| 2010/0121257 A1 | 5/2010 | King | |
| 2010/0126268 A1 | 5/2010 | Baily et al. | |
| 2010/0191178 A1 | 7/2010 | Ross et al. | |
| 2010/0211030 A1 | 8/2010 | Turner et al. | |
| 2010/0280435 A1 | 11/2010 | Raney et al. | |
| 2010/0280536 A1 | 11/2010 | Hartwell | |
| 2010/0305523 A1 | 12/2010 | Vess | |
| 2010/0318043 A1 | 12/2010 | Malhi et al. | |
| 2010/0318071 A1 | 12/2010 | Wudyka | |
| 2011/0015587 A1 | 1/2011 | Tumey et al. | |
| 2011/0038741 A1 | 2/2011 | Lissner et al. | |
| 2011/0054810 A1 | 3/2011 | Turner et al. | |
| 2011/0063117 A1 | 3/2011 | Turner et al. | |
| 2011/0066110 A1 | 3/2011 | Fathallah et al. | |
| 2011/0071415 A1 | 3/2011 | Karwoski et al. | |
| 2011/0092927 A1 | 4/2011 | Wilkes et al. | |
| 2011/0106028 A1 | 5/2011 | Giezendanner et al. | |
| 2011/0130712 A1 | 6/2011 | Topaz | |
| 2011/0178481 A1 | 7/2011 | Locke et al. | |
| 2011/0196321 A1 | 8/2011 | Wudyka | |
| 2011/0251569 A1 | 10/2011 | Turner et al. | |
| 2011/0257572 A1 | 10/2011 | Locke et al. | |
| 2012/0001762 A1 | 1/2012 | Turner et al. | |
| 2012/0035560 A1 | 2/2012 | Eddy et al. | |
| 2012/0046625 A1 | 2/2012 | Johannison | |
| 2012/0123323 A1 | 5/2012 | Kagan et al. | |
| 2012/0123358 A1 | 5/2012 | Hall et al. | |
| 2012/0181405 A1 | 7/2012 | Zlatic et al. | |
| 2012/0184930 A1 | 7/2012 | Johannison | |
| 2012/0184932 A1 | 7/2012 | Giezendanner et al. | |
| 2012/0209226 A1 | 8/2012 | Simmons et al. | |
| 2012/0220960 A1 | 8/2012 | Ruland | |
| 2012/0226247 A1 | 9/2012 | Danei et al. | |
| 2012/0259283 A1 | 10/2012 | Haase | |
| 2012/0271256 A1 | 10/2012 | Locke et al. | |
| 2012/0289895 A1 | 11/2012 | Tsoukalis | |
| 2012/0289913 A1 | 11/2012 | Eckstein et al. | |
| 2013/0144227 A1 | 6/2013 | Locke et al. | |
| 2013/0165877 A1 | 6/2013 | Leeson et al. | |
| 2013/0267918 A1 | 10/2013 | Pan et al. | |
| 2014/0100516 A1 | 4/2014 | Hunt et al. | |
| 2014/0114236 A1 | 4/2014 | Gordon | |
| 2014/0114237 A1 | 4/2014 | Gordon | |
| 2014/0163490 A1 | 6/2014 | Locke et al. | |
| 2014/0194835 A1 | 7/2014 | Ehlert | |
| 2014/0303551 A1 | 10/2014 | Germain et al. | |
| 2014/0323906 A1 | 10/2014 | Peatfield et al. | |
| 2015/0094673 A1 | 4/2015 | Pratt et al. | |
| 2015/0094674 A1 | 4/2015 | Pratt et al. | |

(56) References Cited

U.S. PATENT DOCUMENTS

| | | | |
|---|---|---|---|
| 2015/0290364 A1 | 10/2015 | Wall et al. | |
| 2016/0184496 A1 | 6/2016 | Childress et al. | |
| 2017/0065751 A1 | 3/2017 | Toth | |

FOREIGN PATENT DOCUMENTS

| | | | |
|---|---|---|---|
| GB | 2501256 | 10/2013 | |
| WO | WO-9619335 A1 | 6/1996 | |
| WO | WO-2008036344 A1 | 3/2008 | |
| WO | WO-2008039223 A1 | 4/2008 | |
| WO | WO-2008039314 A2 | 4/2008 | |
| WO | WO-2008048481 A2 | 4/2008 | |
| WO | WO-2011107972 A1 | 9/2011 | |
| WO | WO-2011124388 A1 | 10/2011 | |
| WO | WO-2012009869 A1 | 1/2012 | |
| WO | WO 2012/027913 | 3/2012 | |
| WO | WO-2012027914 A1 | 3/2012 | |
| WO | WO-2012027915 A1 | 3/2012 | |
| WO | WO-2012027916 A1 | 3/2012 | |
| WO | WO-2012078784 A1 | 6/2012 | |
| WO | WO-2013029330 A1 | 3/2013 | |
| WO | WO-2013063848 A1 | 5/2013 | |
| WO | WO 2014/151930 | 9/2014 | |
| WO | WO-2014151930 A2 * | 9/2014 | .......... A61M 1/0086 |
| WO | WO-2015137126 A1 | 9/2015 | |
| WO | WO-2016018448 A1 | 2/2016 | |
| WO | WO-2017139686 A1 | 8/2017 | |
| WO | WO-2018148017 A1 | 8/2018 | |
| WO | WO-2018148487 A1 | 8/2018 | |

OTHER PUBLICATIONS

International Preliminary Report on Patentability for Application No. PCT/US2017/017538, dated Aug. 23, 2018, 12 pages.
Invitation to Pay Additional Fees and Partial Search Report, re PCT Application No. PCT/US2017/017538, dated May 3, 2017.
International Search Report and Written Opinion, re PCT Application No. PCT/US2017/017538, dated Jul. 19, 2017.

* cited by examiner

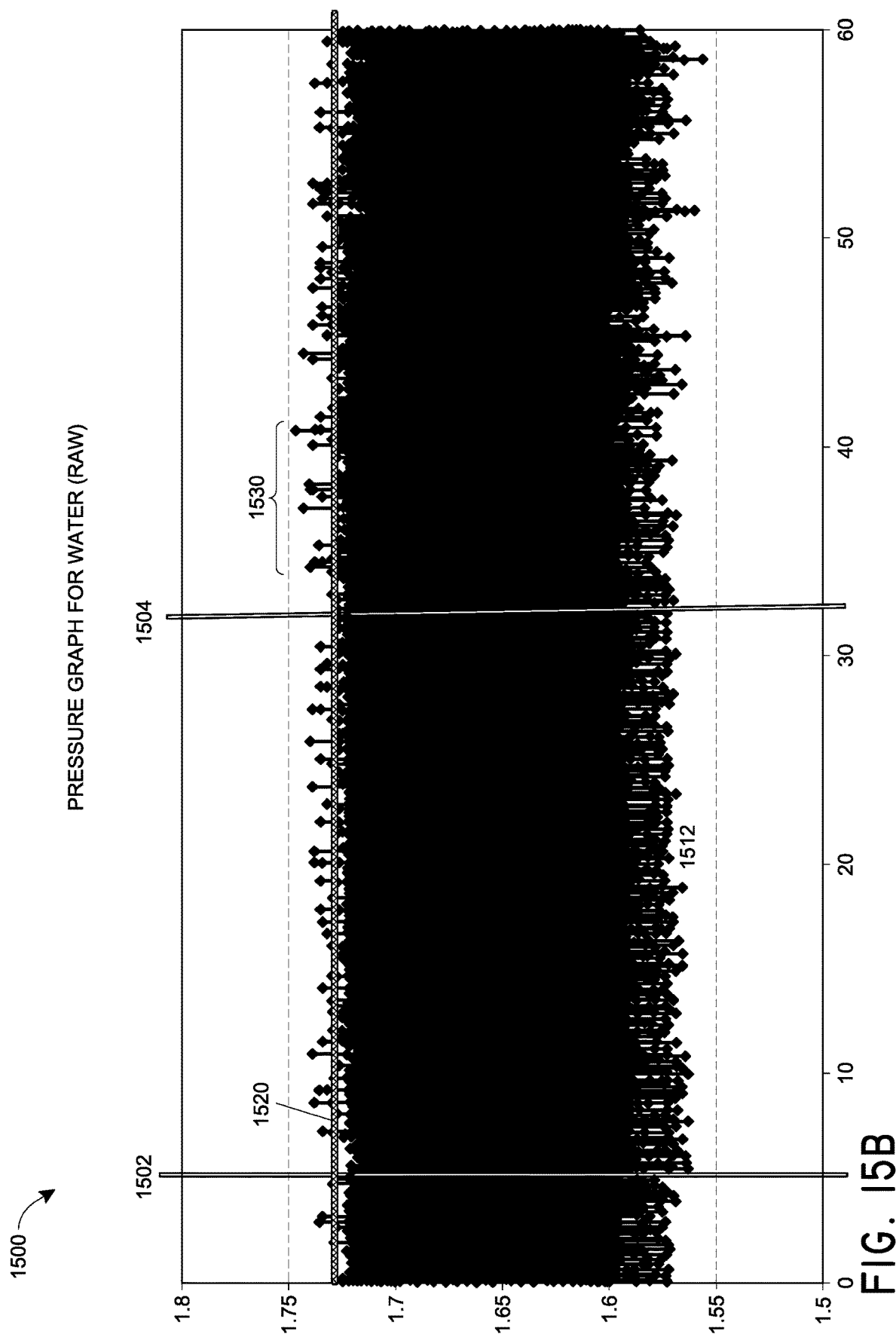

SYSTEMS AND METHODS FOR DETECTING OPERATIONAL CONDITIONS OF REDUCED PRESSURE THERAPY

CROSS-REFERENCE TO RELATED APPLICATIONS

The present application is a U.S. National Stage application of International Application No. PCT/US2017/017538, filed on Feb. 10, 2017, which claims the benefit of U.S. Provisional Patent Application No. 62/294,725, filed on Feb. 12, 2016; U.S. Provisional Patent Application No. 62/294,816, filed on Feb. 12, 2016; and U.S. Provisional Patent Application No. 62/305,475, filed on Mar. 8, 2016, each of which is incorporated by reference in its entirety.

BACKGROUND

Field

Embodiments of the present disclosure relate to systems and methods for dressing and treating a wound with reduced pressure therapy, negative pressure wound therapy (NPWT), or topical negative pressure therapy (TNP). In particular, but without limitation, embodiments of this disclosure relate to negative pressure therapy devices, methods for controlling the operation of TNP systems, and methods of using TNP systems.

Description of the Related Art

Embodiments of the present disclosure relate to apparatuses and methods for dressing and treating a wound with reduced pressure therapy. In particular, but without limitation, embodiments disclosed herein relate to negative pressure therapy devices, methods for controlling the operation of TNP systems, and methods of using TNP systems.

SUMMARY

In some embodiments, an apparatus for applying negative pressure to a wound includes a negative pressure source disposed in a housing, the negative pressure source configured to be coupled, via a fluid flow path including at least one lumen, to a dressing placed over a wound and to provide negative pressure to the dressing, one or more pressure sensors configured to monitor a pressure in the fluid flow path. The apparatus also includes a controller configured to while the negative pressure source provides negative pressure, detect presence of blood in the fluid flow path based at least on the pressure monitored by the one or more pressure sensors, and in response to detecting presence of blood in the fluid flow path, provide an indication of presence of blood.

The apparatus of preceding paragraph can include one or more of the following features. The indication can be prevention of administration of negative pressure to the wound dressing by at least one of deactivating operation of the negative pressure source, opening a vent positioned in the fluid flow path or closing a valve positioned in the fluid flow path. The controller can be configured to detect presence of blood in a canister based at least on data from one or more optical sensors. The one or more pressure sensors can include at least two pressure sensors. The indication can include activation of an audible or visible alarm. The controller can be configured to detect presence of blood further based on a level of activity of the negative pressure source. The controller can be configured to determine the level of activity based on at least one of a duty cycle signal of the negative pressure source or a tachometer signal.

In some embodiments, an apparatus for applying negative pressure to a wound includes a negative pressure source disposed in a housing, the negative pressure source configured to be coupled, via a fluid flow path including at least one lumen, to a dressing configured to be placed over a wound and to provide negative pressure to the dressing and one or more pressure sensors configured to monitor a pressure in the fluid flow path. The apparatus also includes a controller configured to while the negative pressure source provides negative pressure to the dressing, determine an estimated flow rate of a substance aspirated from the wound into the fluid flow path based at least on the pressure monitored by the one or more pressure sensors, and store, in a memory device, a flow rate value indicative of the estimated flow rate of the substance.

The apparatus of any of preceding paragraphs can include one or more of the following features. The controller can be configured to output the flow rate value. The controller can be configured to activate one of a first flow rate indicator or second flow rate indicator responsive to the flow rate value, the first flow rate indicator denoting a change in at least one fluid parameter of the substance aspirated from the wound than the second flow rate indicator. At least one fluid parameter can include density of the substance. The controller can be configured to determine the estimated flow rate of the substance based at least on one or more of (i) a rate of change of the pressure monitored by the one or more pressure sensors, (ii) a duration that the pressure monitored by the one or more pressure sensors remains at a level, (iii) a mode of operation of the controller or the negative pressure source, (iv) a level of activity of the negative pressure source, (v) a flow rate measured in the fluid flow path by a flow rate detector, (vi) a flow rate in the fluid flow path calculated by the controller, or (vii) a mass flow in the fluid flow path calculated by the controller. The controller can be configured to determine a confidence value associated with the estimated flow rate, the confidence value being indicative of an estimated accuracy of the estimated flow rate relative to an actual flow rate of the substance. The controller can be configured to activate one of a first confidence indicator or second confidence indicator responsive to the confidence value, the first confidence indicator denoting a higher confidence than the second confidence indicator. The controller can be configured to modify operation of the negative pressure source responsive to at least one of the flow rate value or the confidence value.

In some embodiments, an apparatus for applying negative pressure to a wound includes a negative pressure source configured to provide negative pressure, via a fluid flow path, to a dressing placed over a wound and one or more pressure sensors configured to monitor a pressure in the fluid flow path. The apparatus also includes a controller configured to detect presence of blood in the fluid flow path based on the pressure monitored by the one or more pressure sensors and an activity level of the negative pressure source, and provide an indication that blood is present in the fluid flow path.

The apparatus of any of preceding paragraphs can include one or more of the following features. The negative pressure source can be a pump operated by an actuator, and wherein the activity level includes at least one of a pump speed, a pulse width modulation (PWM) signal configured to drive the actuator, or a current signal configured to drive the actuator. The controller can be configured to compute a first indicator associated with change in the pressure over a time duration and a second indicator associated with change in the activity level over the time duration; and detect presence of blood based on the first and second indicators. At least one of the first or second indicators can be a statistical indicator. The controller can be configured to perform a time series analysis to determine if at least one of the first or second indicators deviates from a threshold and based on the deviation detect presence of blood. Time series analysis can include determination of a cumulative sum (Cusum) of at least one of the first or second indicators. Cusum of at least one of the first or second indicators can include a sliding causal Cusum. The first indicator can include mean pressure over the time duration and the second indicator includes standard deviation of standard deviation of the current signal over the time duration. The indication that blood is present in the fluid flow path can include one or more of: activation of an alarm, release of negative pressure in the fluid flow path, decrease of a target negative pressure provided by the negative pressure source, or deactivation of the negative pressure source.

The apparatus of any of preceding paragraphs can include one or more of the following features. The controller can be configured to detect and provide indication of one or more of: presence of water in the fluid flow path, presence of exudate in the fluid flow path, presence of gas leak in the fluid flow path, or change in the pressure in the fluid flow path. The controller can be configured to compute a plurality of indicators associated with change in the pressure over a time duration and change in the activity level over the time duration; and detect and provide an indication of one or more of presence of water in the fluid flow path, presence of exudate in the fluid flow path, presence of gas leak in the fluid flow path, or change in the pressure in the fluid flow path based on the plurality of indicators. At least some of the plurality of indicators can include a statistical indicator. The controller can be configured to perform a time series analysis to determine if at least some of the plurality of indicators deviate from one or more thresholds and based on the deviation detect one or more of presence of water in the fluid flow path, presence of exudate in the fluid flow path, presence of gas leak in the fluid flow path, or change in negative pressure in the fluid flow path. Time series analysis can include determination of a cumulative sum (Cusum) of at least some of the plurality of indicators. Cusum of at least some of the plurality of indicators can include a sliding causal Cusum. An indicator associated with change in the pressure in the fluid flow path can include mean pressure over the time duration, an indicator associated with presence of gas leak in the fluid flow path includes standard deviation of a mean of the current signal, and an indicator associated with presence of water or exudate in the fluid flow path includes kurtosis of standard deviation of the pump speed. The controller is can be configured to determine malfunction of the one or more pressure sensors based on at least one of the indicators.

In some embodiments, a method of operating an apparatus for applying negative pressure to a wound includes while providing negative pressure from a negative pressure source of the apparatus, via a fluid flow path, to a wound dressing configured to be placed over the wound, detecting presence of blood in the fluid flow path based at least on a pressure in the fluid flow path, and in response to detecting presence of blood in the fluid flow path, providing an indication of presence of blood.

The method of preceding paragraph can include one or more of the following features. Providing the indication can include preventing administration of negative pressure to the wound dressing by at least one of deactivating operation of the negative pressure source, opening a vent positioned in the fluid flow path or closing a valve positioned in the fluid flow path. Detecting presence of blood in a canister can be based at least on data from one or more optical sensors. The method can include activating of an audible or visible alarm in response to detecting presence of blood in the fluid flow path. The method can include detecting presence of blood based on a level of activity of the negative pressure source. The method can include determining the level of activity based on at least one of a duty cycle signal of the negative pressure source or a tachometer signal.

In some embodiments, a method of operating an apparatus for applying negative pressure to a wound includes while providing negative pressure from a negative pressure source of the apparatus, via a fluid flow path, to a wound dressing configured to be placed over the wound, determining an estimated flow rate of a substance aspirated from the wound into the fluid flow path based at least on a pressure in the fluid flow path, and outputting the flow rate value.

The method of any of preceding paragraphs can include one or more of the following features. The method can include activating one of a first flow rate indicator or second flow rate indicator responsive to the flow rate value, the first flow rate indicator denoting a change in at least one fluid parameter of the substance aspirated from the wound than the second flow rate indicator. At least one fluid parameter can include density of the substance. Determining the estimated flow rate of the substance can be based at least on one or more of (i) a rate of change of the pressure in the fluid flow path, (ii) a duration that the pressure in the fluid flow path remains at a level, (iii) a mode of operation of a controller of the apparatus or the negative pressure source, (iv) a level of activity of the negative pressure source, (v) a flow rate in the fluid flow path measured by a flow rate detector, (vi) a flow rate in the fluid flow path calculated by the controller, or (vii) a mass flow in the fluid flow path calculated by the controller. The method can include determining a confidence value associated with the estimated flow rate, the confidence value being indicative of an estimated accuracy of the estimated flow rate relative to an actual flow rate of the substance. The method can include activating one of a first confidence indicator or second confidence indicator responsive to the confidence value, the first confidence indicator denoting a higher confidence than the second confidence indicator. The method can include modifying operation of the negative pressure source responsive to at least one of the flow rate value or the confidence value.

In some embodiments, a method of operating an apparatus for applying negative pressure to a wound includes providing negative pressure from a negative pressure source of the apparatus, via a fluid flow path, to a wound dressing configured to be placed over the wound, detecting presence of blood in the fluid flow path based on a pressure monitored in the fluid flow path and an activity level of the negative pressure source, and providing an indication that blood is present in the fluid flow path.

The method of any of preceding paragraphs can include one or more of the following features. Negative pressure source can include a pump operated by an actuator, and the activity level can include at least one of a pump speed, a pulse width modulation (PWM) signal configured to drive the actuator, or a current signal configured to drive the actuator. The method can include computing a first indicator associated with change in the pressure over a time duration and a second indicator associated with change in the activity level over the time duration, and detecting presence of blood based on the first and second indicators. At least one of the first or second indicators can include a statistical indicator. The method can include performing a time series analysis to determine if at least one of the first or second indicators deviates from a threshold and based on the deviation detect presence of blood. Time series analysis can include determination of a cumulative sum (Cusum) of at least one of the first or second indicators. Cusum of at least one of the first or second indicators can include a sliding causal Cusum. The first indicator can include mean pressure over the time duration and the second indicator includes standard deviation of standard deviation of the current signal over the time duration.

The method of any of preceding paragraphs can include one or more of the following features. The indication that blood is present in the fluid flow path can include one or more of: activation of an alarm, release of negative pressure in the fluid flow path, decrease of a target negative pressure provided by the negative pressure source, or deactivation of the negative pressure source. The method can include detecting and providing indication of one or more of: presence of water in the fluid flow path, presence of exudate in the fluid flow path, presence of gas leak in the fluid flow path, or change in the pressure in the fluid flow path. The method can include computing a plurality of indicators associated with change in the pressure over a time duration and change in the activity level over the time duration, and detecting and providing an indication of one or more of presence of water in the fluid flow path, presence of exudate in the fluid flow path, presence of gas leak in the fluid flow path, or change in the pressure in the fluid flow path based on the plurality of indicators. At least some of the plurality of indicators can include a statistical indicator. The method can include performing a time series analysis to determine if at least some of the plurality of indicators deviate from one or more thresholds and based on the deviation detect one or more of presence of water in the fluid flow path, presence of exudate in the fluid flow path, presence of gas leak in the fluid flow path, or change in negative pressure in the fluid flow path. Time series analysis can include determination of a cumulative sum (Cusum) of at least some of the plurality of indicators. Cusum of at least some of the plurality of indicators can include a sliding causal Cusum. An indicator associated with change in the pressure in the fluid flow path can include mean pressure over the time duration. An indicator associated with presence of gas leak in the fluid flow path can include standard deviation of a mean of the current signal. An indicator associated with presence of water or exudate in the fluid flow path can include kurtosis of standard deviation of the pump speed. The method can include determining malfunction of a pressure sensor of the apparatus based on at least one of the indicators.

BRIEF DESCRIPTION OF THE DRAWINGS

Embodiments of the present disclosure will now be described hereinafter, by way of example only, with reference to the accompanying drawings in which:

FIGS. 15A-B illustrate vacuum pressure data according to some embodiments.

DETAILED DESCRIPTION

Figure 1:
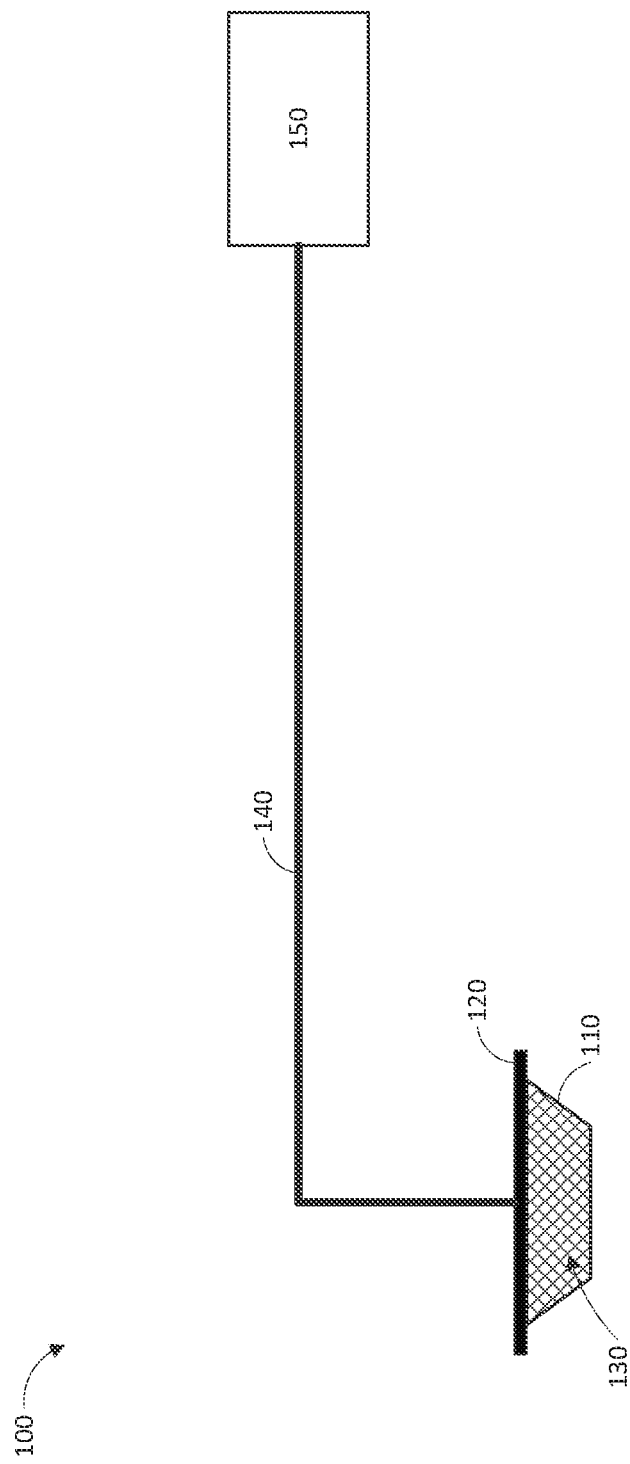
FIG. 1 illustrates a negative pressure wound therapy system according to some embodiments.

The present disclosure relates to methods and apparatuses for dressing and treating a wound with reduced pressure therapy or topical negative pressure (TNP) therapy. The methods, apparatuses, and devices can incorporate or implement any combination of the features described below.

Overview

Embodiments disclosed herein relate to systems and methods of treating a wound with reduced pressure. As is used herein, reduced or negative pressure levels, such as −X mmHg, represent pressure levels relative to ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below, for example, 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in in topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, and/ or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

In certain embodiments, a negative pressure wound therapy system can detect and classify one or more operational conditions, including detection of a wound bleeding. The ability to detect blood, particularly a bleed out, may be safety critical and prevent harm (such as, pain or discomfort) to a patient, and may be used to prevent exsanguination (e.g., particularly for deeper wounds). The system can react to detection of blood by providing an indication (e.g., high priority alarm), reducing the intensity or stopping therapy, releasing negative pressure, and the like.

In some embodiments, the system can detect one or more additional operational conditions, such as change in vacuum pressure, gas leak rate change, exudate flow rate change, water flow rate change, presence of exudate, presence of water, and the like. The system can detect and distinguish between (or classify) different operational conditions and provide indication or take remedial action.

Negative Pressure System

FIG. 1 illustrates an embodiment of a negative or reduced pressure wound treatment (or TNP) system 100 including a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a negative pressure device or pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless device (meaning that exudate is collected in the wound dressing). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity at atmospheric pressure, and also may have a substantially reduced compressed volume when under negative pressure. The wound cover 120 can provide a substantially fluid impermeable seal over the wound cavity 110. In some embodiments, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material.

Some embodiments of the wound cover 120 can have a port (not shown) configured to receive an end of the conduit 140. In some embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. In some embodiments, though not required, the pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

Some embodiments of the system 100 are designed to operate without the use of an exudate canister. Some embodiments of the system 100 can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump assembly.

In some embodiments, the pump assembly 150 can be configured to deliver negative pressure at a desired negative pressure setpoint or target pressure, which can be selected or programmed to be approximately −80 mmHg, or between about −20 mmHg and −200 mmHg (e.g., as selected by a user). Note that these pressures are relative to normal ambient atmospheric pressure thus, −200 mmHg would be about 560 mmHg assuming that ambient atmospheric pressure is 760 mmHg. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even −150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below 200 mmHg. Intermittent therapy can be delivered between low and high negative pressure set points or target pressures. Low set point can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high set points and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys Aft Renasys Soft Port, and Pico Dressings available from Smith & Nephew. Further description of such wound dressings and other components of a negative pressure wound therapy system that may be used with the pump assembly and other embodiments of the present application are found in U.S. Pat. Nos. 8,801,685, 8,791,315, 9,061,095, 8,905,985, 9,084,845; U.S. Patent Publication Nos. 2015/0025482 and 2016/0136339; and International Patent Publication No. WO 2016/018448, each of which is incorporated by reference in its entirety. In other embodiments, other suitable wound dressings can be utilized.

Figure 2:
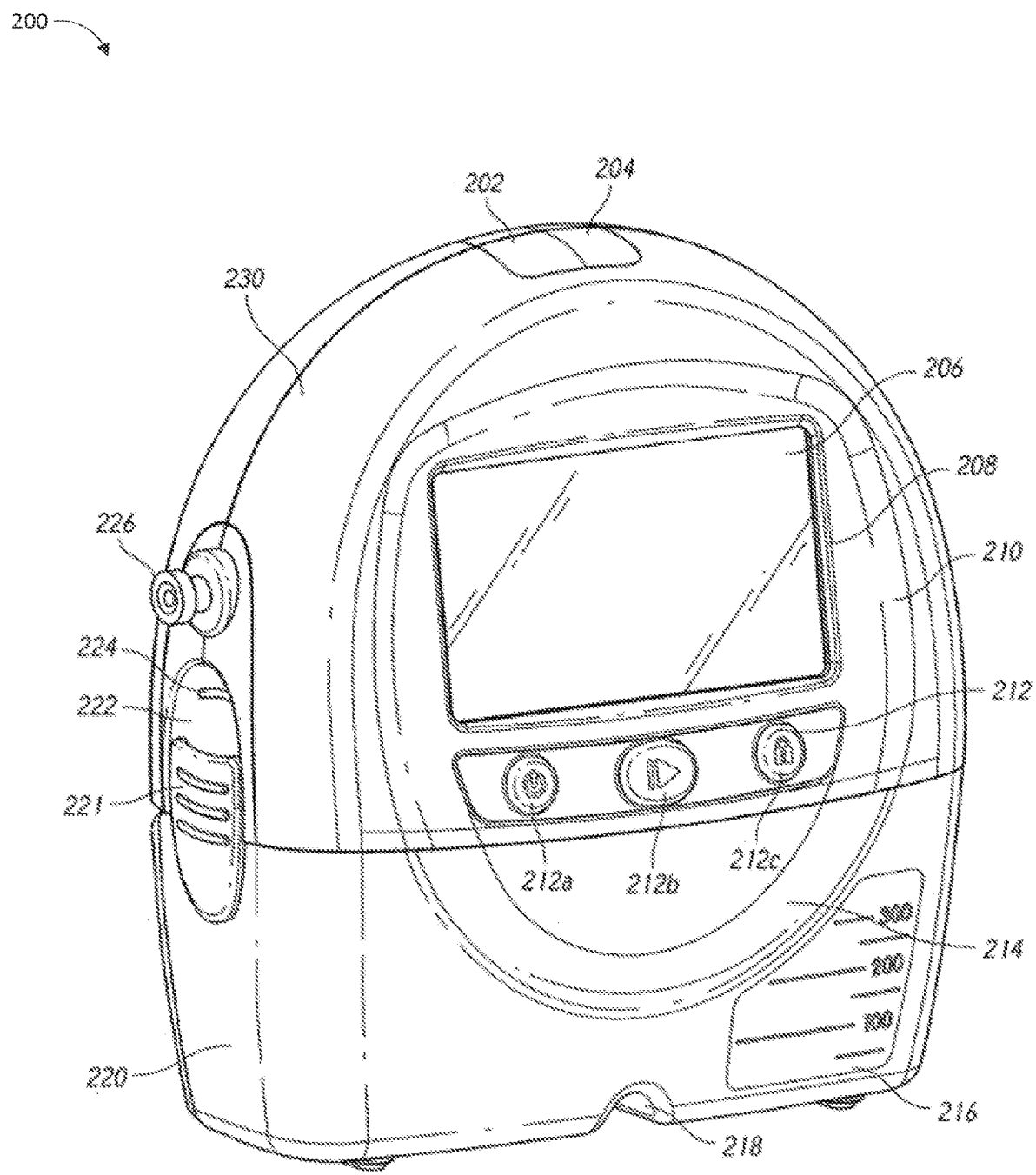
FIG. 2 illustrates a negative pressure wound therapy device according to some embodiments.

FIG. 2 illustrates a negative pressure wound therapy device 200 according to some embodiments. The device includes a pump assembly 230 and a canister 220. As is illustrated, the pump assembly 230 and the canister are connected, thereby forming a device. The pump assembly 230 comprises one or more indicators, such as visual indicator 202 configured to indicate alarms and visual indicator 204 configured to indicate status of the TNP system. The indicators 202 and 204 can be configured to alert a user, such as patient or medical care provider, to a variety of operating parameters and/or failure conditions of the negative pressure system, including alerting the user to normal or proper operational conditions, pump failure, power supplied to the pump or power failure, detection of a leak within the wound cover or flow pathway, suction blockage, unexpected change in pressure, bleeding, or any other similar or suitable conditions or combinations thereof. The pump assembly 230 can comprise additional indicators. The pump assembly can use a single indicator or multiple indicators. Any suitable indicator can be used such as one or more of visual, audio, tactile, and so on. The indicator 202 can be configured to signal alarm conditions, such as canister full, system blockage, power low, conduit 140 disconnected, seal broken in the wound seal 120, blood detected, and so on. The indicator 202 can be configured to display colored flashing and/or continuous light (e.g. red, amber, green or blue and combinations thereof) to draw user's attention. The indicator 204 can be configured to signal status of the TNP system, such as therapy delivery is ok, leak detected, exudate detected, water detected, another type of fluid detected, and so on. The indicator 204 can be configured to display one or more different colors of light, such as green, yellow, red, etc. For example, green light can be emitted when the TNP system is operating properly and yellow light can be emitted to indicate a warning. In some embodiments, indicators 202 and 204 can be interchangeable or redundant.

The pump assembly 230 comprises a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 comprises one or more keys or buttons 212 configured to allow the user to operate and monitor the operation of the TNP system. As is illustrated, three buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 and/or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses and/or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises a gas outlet 224 for allowing gas removed from the wound cavity 110 to escape. Gas entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted and/or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted and/or various additional features are added to the canister 220. Any of the disclosed canisters may include or may omit a solidifier.

Figure 3:
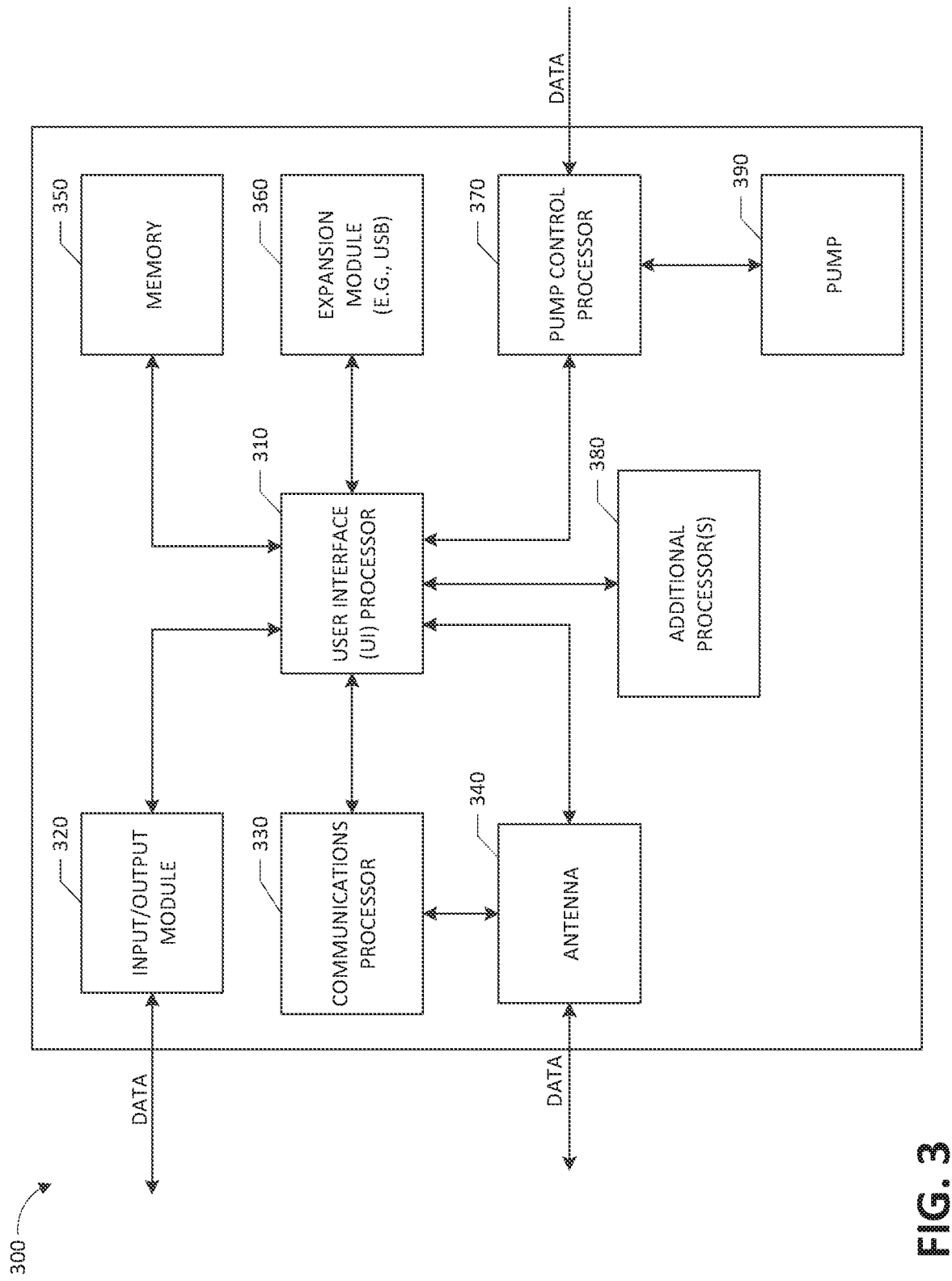
FIG. 3 illustrates an electrical component schematic of a negative pressure wound therapy device according to some embodiments.

FIG. 3 illustrates an electrical component schematic 300 of a negative pressure device or pump assembly, such as the pump assembly 150, according to some embodiments. Electrical components can operate to accept user input, provide output to the user, operate the pump assembly and the negative pressure system, provide network connectivity, and so on. Electrical components can be mounted on one or more printed circuit boards (PCBs). As is illustrated, the pump assembly can include multiple processors or controllers. It may be advantageous to utilize multiple processors in order to allocate or assign various tasks to different processors. A first processor can be responsible for user activity and a second processor can be responsible for controlling the pump. This way, the activity of controlling the pump, which may necessitate a higher level of responsiveness (corresponding to higher risk level), can be offloaded to a dedicated processor and, thereby, will not be interrupted by user interface tasks, which may take longer to complete because of interactions with the user. In some embodiments, the pump assembly can include less or more processors than illustrated in FIG. 3.

The pump assembly can comprise a user interface processor or controller 310 configured to operate one or more components for accepting user input and providing output to the user, such as a display, button(s), speaker(s), indicator(s), etc. Input to the pump assembly and output from the pump assembly can be controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal and/or external to the processor 310. Any suitable type of memory can be used, including volatile and/or non-volatile memory, such as RAM, ROM, magnetic memory, solid-state memory, Magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling a display 206, processor for controlling one or more buttons, etc.). The processor 310 can run a suitable operating system, such as a Linux, Windows CE, VxWorks, etc. One or more of the processors described herein can be a DSP processor.

The pump control processor 370 can be configured to control the operation of a negative pressure pump 390. The pump 390 can be a suitable pump, such as a diaphragm pump, peristaltic pump, rotary pump, rotary vane pump, scroll pump, screw pump, liquid ring pump, pump (for example, diaphragm pump) operated by a piezoelectric transducer, voice coil pump, and the like. The pump control processor 370 can measure pressure in a fluid flow path, using data received from one or more pressure sensors (which can be positioned anywhere in the flow path), calculate the rate of fluid flow, and control the pump. The pump control processor 370 can control an actuator (e.g., pump motor) so that a desired level of negative pressure is achieved in the wound cavity 110. The desired level of negative pressure can be pressure set or selected by the user. In various embodiments, the pump control processor 370 controls an actuator of the pump (for example, a pump motor) using pulse-width modulation (PWM) or another suitable drive signal. A control signal for driving the pump can be a 0-100% duty cycle PWM signal. The pump control processor 370 can perform flow rate calculations and detect various conditions in a flow path. The pump control processor 370 can communicate information to the processor 310. The pump control processor 370 can include internal memory and/or can utilize memory 350. The pump control processor 370 can be a low-power processor.

A communications processor 330 can be configured to provide wired and/or wireless connectivity to another computing device, such as a remote monitoring station. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. The communications processor 330 can provide dual GPS/cellular functionality. Cellular functionality can, for example, be 3G functionality. In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. The pump assembly can include a SIM card, and SIM-based positional information can be obtained.

The communications processor 330 can communicate information to the processor 310. The communications processor 330 can include internal memory and/or can utilize memory 350. The communications processor 330 can be a low-power processor.

In some embodiments, the pump assembly can track and store various data, such as one or more of positioning data, therapy parameters, logs, device data, and so on. The pump assembly can track and log therapy and other operational data. Data can be stored, for example, in the memory 350.

In some embodiments, using the connectivity provided by the communications processor 330, the device can upload any of the data stored, maintained, and/or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. The pump assembly can provide Internet browsing functionality using one or more browser programs, mail programs, application software (e.g., apps), etc.

In some embodiments, the communications processor 330 can use the antenna 340 to communicate a location of the pump assembly, such as a location of a housing of the pump assembly, to other devices in the proximity (for example, within 10, 20, or 50 meters and the like) of the pump assembly. The communications processor 330 can perform one-way or two-way communication with the other devices depending on the implementation. The communications transmitted by the communications processor 330 can include identifying information to uniquely identify the pump assembly relative to one or more other pump assemblies also in the proximity of the pump assembly. For example, identifying information can include a serial number or a value derived from the serial number. The signal strength of the transmitted communications by the communications processor 330 can be controlled (for example, maintained at a constant or substantially constant level) to enable another device to determine a distance to the pump assembly, such as a distance between the device and the pump assembly.

In some embodiments, the communications processor 330 can communicate with other devices in the proximity of the pump assembly so that the communications processor 330 can itself determine a distance from the pump assembly to the other devices. The communications processor 330, in such embodiments, can track and store the distance from the pump assembly to the other devices or indications of change in the distance over time, and the communications processor 330 can later provide this information to the other devices. For instance, the communications processor 330 can determine a duration of time during which the pump assembly has been removed from a coverage area of a device and subsequently report this time to the device upon being returned to the coverage area.

Detection of Operational Conditions

In some embodiments, negative pressure wound therapy system can monitor and detect operational conditions of the negative pressure system, such as the system 100 in FIG. 1. Operational conditions can include changes in pressure, fluid leaks (including change in gas flow rate, change in water flow rate, change in exudate flow rate), presence of blood, blockages, and the like. Water can include substances that consist mainly of water, such as physiological solutions having up to 90% (or more or less) water. These substances can include physiological saline, wound washes, ringer's solutions, wound irrigants, antibiotics, or any other aqueous based solution of compounds used in the treatment of wounds (e.g., having a dynamic viscosity 0.7 to 1.3 mPa s (millipascal seconds) at 25° C. or any other suitable viscosity and specific gravity in the range of 0.95 to 1.1).

In some embodiments, the system can classify or distinguish a particular operational condition from other conditions. As explained herein, the system can detect a change in properties of fluid that flows through the fluid flow path and determine a type of fluid causing the change (e.g., blood, exudate, water, etc.). For example, flow rate can be one of fluid properties, and the system can detect a change in the flow rate (e.g., relative to one or more thresholds) and classify the fluid type. Flow rate can change due to introduction into the flow path of fluid that has different properties (e.g., density or viscosity). The system can detect a change in properties of the fluid in the fluid flow path and classify the change to determine the fluid type. In some implementations, the system can detect a change in flow due to changes in dimensions of the flow path (e.g., decrease in diameter due to a restriction or blockage, increase in diameter due to removal of restriction or blockage, etc.), surface tension, gravitational force (e.g., patient raises a limb which has a wound, stands up, etc.), and the like.

During the provision of TNP therapy, different substances, such as gas (e.g., air), exudate, water, blood, and tissue aspirated from the wound cavity 110 may enter the fluid flow path (including any one or more of dressing, tube or lumen 140, or canister) in the system 100 of FIG. 1. The pump assembly 150 can desirably, in certain embodiments, determine a one or more properties of one or more substances in the fluid flow path so that the pump assembly 150 can determine a composition or properties of the substance and enable one or more appropriate actions to be taken in view of the composition or properties of the substance. For example, because blood may be denser and differ in viscosity than liquid or gaseous exudate, blood can be differentiated from exudate, among other possible substances, by monitoring one or more operational parameters of the system, such as pressure, activity, and the like, and determining presence of one or more substances in the fluid flow path. For example, the system can determine that the composition of the aspirated substance has one or more properties that satisfy one or more thresholds. The ability to detect blood, particularly a bleed out, may be safety critical and prevent harm (such as, pain, discomfort, or death) to a patient, and may be used to prevent exsanguination in worst cases (e.g., particularly for deeper wounds and wounds where major blood vessels may be exposed, close to the surface of the tissue, or damaged).

Figure 4:
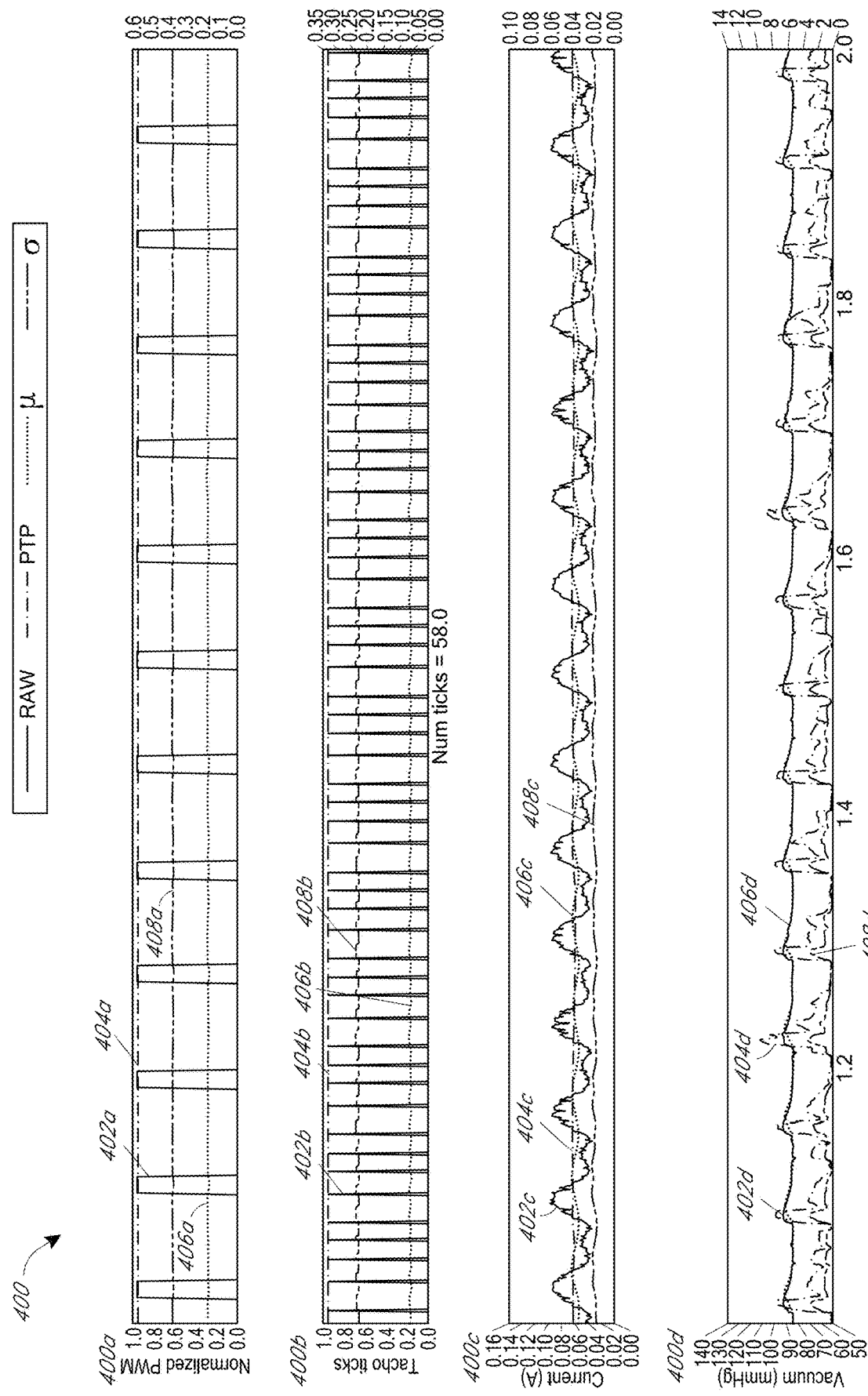
FIG. 4 illustrates operational parameters according to some embodiments.

FIG. 4 illustrates operational parameters 400 that can be used for detecting one or more operational conditions according to some embodiments. These parameters can include pressure measurements, level of activity measurements, and the like obtained during operation of the negative pressure wound therapy system. Parameters 400 can correspond to the system operating under a particular negative pressure setting (such as −80 mmHg) and a particular gas leak (such as 60 standard cubic centimeter per minute (sccm)).

In some embodiments, the level of activity can include one or more parameters of an actuator (e.g., motor) of the negative pressure source, such as current (or voltage) of a motor drive signal, PWM signal, and motor speed. These parameters are illustrated in FIG. 4. Graph 400a illustrates PWM signal 402a for driving the motor captured over a time period, such as 1 second or another suitable time period. Also illustrated is a peak-to-peak 404a of the PWM signal, average or mean of the PWM signal 406a, and standard deviation 408a of the PWM signal. Graph 400b illustrates motor or pump speed 402b, which can be determined using a Hall sensor, tachometer, or another suitable sensor. Motor speed can be represented as partial or full pump motor rotations (e.g., for diaphragm pump) or may be an account or a measure of piston/diaphragm displacement (e.g., for a reciprocating pump). Signal 402b illustrates timing between tachometer pulses or ticks, with each pulse being represented by an impulse corresponding to a quarter rotation of the pump motor (so that 4 consecutive impulses represent one full revolution of the pump motor). For example, 58 tachometer ticks are illustrated in 400b. Also illustrated is a peak-to-peak 404b of the motor speed signal, mean of the motor speed signal 406b, and standard deviation 408b of the motor speed signal. Graph 400c illustrates motor current signal 402c (e.g., in amperes) for driving the motor captured over a time period, such as 1 second or another suitable time period. Also illustrated is a peak-to-peak 404c of the motor current signal, mean of the motor current signal 406c, and standard deviation 408c of the motor current signal.

Graph 400d illustrates vacuum pressure in the fluid flow path signal 402d (e.g., in mmHg) current captured over a time period, such as 1 second or another suitable time period. Vacuum pressure can be monitored using one or more pressure sensors described herein. Also illustrated is a peak-to-peak 404d of the vacuum pressure signal, mean of the vacuum pressure signal 406d, and standard deviation 408d of the vacuum pressure signal. As is illustrated in FIG. 4, while each signal is approximately periodic, each signal has a different period. These characteristics can be used to detect one or more operational conditions.

In certain embodiments, sampling rate for collecting one or more operational parameters can be chosen to allow detection in parameter changes. For example, sampling rate of at least 0.2 Hz or higher can be used. A sampling rate of 1 kHz was used to collect data in FIG. 4. In some instances, sampling rate of less than 0.2 Hz can be used.

Time Domain Detection and Classification

In some embodiments, time domain analysis can be used to detect and classify one or more operational conditions, such as change in vacuum pressure, detection of blood in the fluid flow path, change in gas (e.g., air) leak rate, change in exudate flow rate, and change in water flow rate. The analysis can include the following:

1) Calculate relevant statistics (and statistics of statistics if applicable) for the input signals;

2) Perform time series analysis to detect when these statistics deviate from norm; and 3) Apply a classification algorithm to analyze the deviations and interpret them as one or more operational conditions.

In some implementations, input signals or operational parameters and their statistics are illustrated in FIG. 4. Time domain analysis can use one or more of the following:

TABLE 1

Input signals and statistics

| Input Signal | Statistic |
|---|---|
| Vacuum Pressure | Raw (e.g., 402d) |
| Vacuum Pressure | Mean (e.g., 406d) |
| Vacuum Pressure | Standard Deviation (e.g., 408d) |
| Vacuum Pressure | Peak to Peak (e.g., 404d) |
| Current | Raw (e.g., 402c) |
| Current | Mean (e.g., 406c) |
| Current | Standard Deviation (e.g., 408c) |
| Current | Peak to Peak (e.g., 404c) |
| PWM | Raw (e.g., 402a) |
| PWM | Mean (e.g., 406a) |
| PWM | Standard Deviation (e.g., 408a) |
| PWM | Peak to Peak (e.g., 404a) |
| Impulse (Motor Speed) | Raw (e.g., 402b) |
| Impulse (Motor Speed) | Mean (e.g., 406b) |
| Impulse (Motor Speed) | Standard Deviation (e.g., 408b) |
| Impulse (Motor Speed) | Peak to Peak (e.g., 404b) |
| Tick Rate (Motor Speed) | Raw (e.g., time between impulses) |

In addition, in some embodiments, statistical properties of one or more of the statistics in Table 1 are calculated. These statistical properties can include one or more of mean, standard deviation, skewness (third statistical moment), kurtosis (fourth statistical moment), minimum, and maximum. A correlation between statistic and signal can be calculated, which determined which statistic(s) are linearly related to which signal. The aim can be to find, for each signal, one statistic that is strongly related to it but is unrelated to the other signals. Such a statistic would thus be a good indicator of when the signal has changed, which can indicate presence of an operational condition. A correlation greater than 0.5 (or less than −0.5) can be indicative of a strong linear relationship.

In some embodiments, to determine whether or not a given statistic is a good fit for a particular signal, three normalized correlations (which by definition are in the range [−1.0, 1.0]) are evaluated via the following equation which measures how distinct that statistic is for a given signal:

$$f_a(c_a, c_b, c_c) = \frac{c_a^2}{\sqrt{c_b^2 + c_c^2}}$$

Where $c_a$ is the coefficient of correlation of the statistic with the variable (or signal) of concern and $c_b$ and $c_c$ are the coefficients of the statistic with the other two input variables (or signals). This equation can be extended to more than three variables by adding additional terms to the denominator. This equation rewards high correlations with the desired variable by squaring the numerator, which also severely penalizes low correlations. The denominator rewards the statistic if it is independent of both other variables (e.g., they are both close to zero). The second norm is used so that one variable being extremely close to zero does not skew the results even if the other variable in the denominator has a fairly high coefficient. The statistic with the highest distinctness as per the above equation can be selected.

In certain implementations, additional or alternative statistics can be used, including the logarithm, exponents, and powers of each of the current statistics as well as their ratios and products. Additional or alternative selection methods to choose the best statistics such Principal Component Analysis (PCA) and Singular Value Decomposition (SVD) can be used. Once the best statistic has been determined, time series analysis algorithms such Auto Regressive Integrated Moving Average (ARIMA), Generalized Autoregressive Conditional Heteroskedasticity (GARCH), or Cusum (or cumulative sum) can be used for detection and classification.

In some embodiments, Cusum can be used to detect and classify one or more operational conditions. Cusum can be defined as the running sum of the difference between each sample and the mean (e.g., in the absence of change, Cusum is zero). Cusum can be used to track variations in the underlying variable.

Cusum can be determined in a number of ways. In certain implementations, non-causal Cusum uses the mean calculated from the entire duration of an input signal, which requires knowledge of all samples before the difference from the mean can be calculated. Non-causal Cusum may not be suitable for real-time monitoring and detection and classification unless an estimate of the mean from prior analysis can be used. Non-causal Cusum can starts and end with a value of zero.

In some instances, sliding causal Cusum can be determined using a sliding window to estimate the mean. Initial step change can yield the first departure from zero, rather than resulting in a change of gradient as in the non-causal Cusum. Sliding causal Cusum can produce data within durations of time that are shorter than with non-causal Cusum. Sliding causal Cusum may allow tighter bounds to be used to detect changes and may be less prone to rounding and rollover errors (e.g., numerical errors that may result from use of longer sequences of data).

In some embodiments, cumulative causal Cusum algorithm uses all preceding samples from the start of a time duration to the current sample to estimate the mean for the current sample. This version of Cusum can be a compromise between the foregoing two versions, and may be smoother than sliding causal Cusum but not ending at a zero value.

Figure 5:
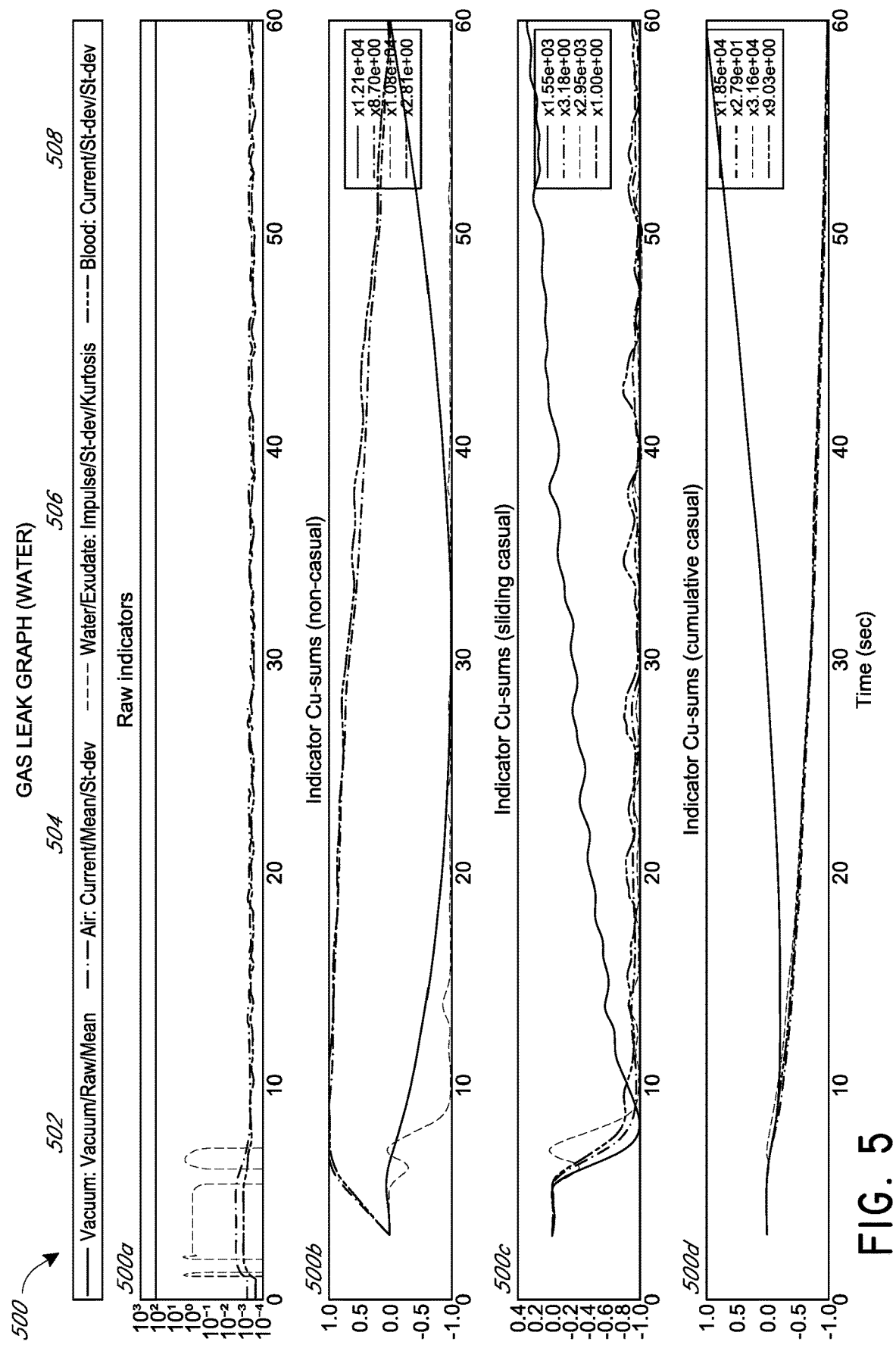
FIG. 5 illustrates detection of a gas leak when water is being aspirated according to some embodiments.
Figure 6:
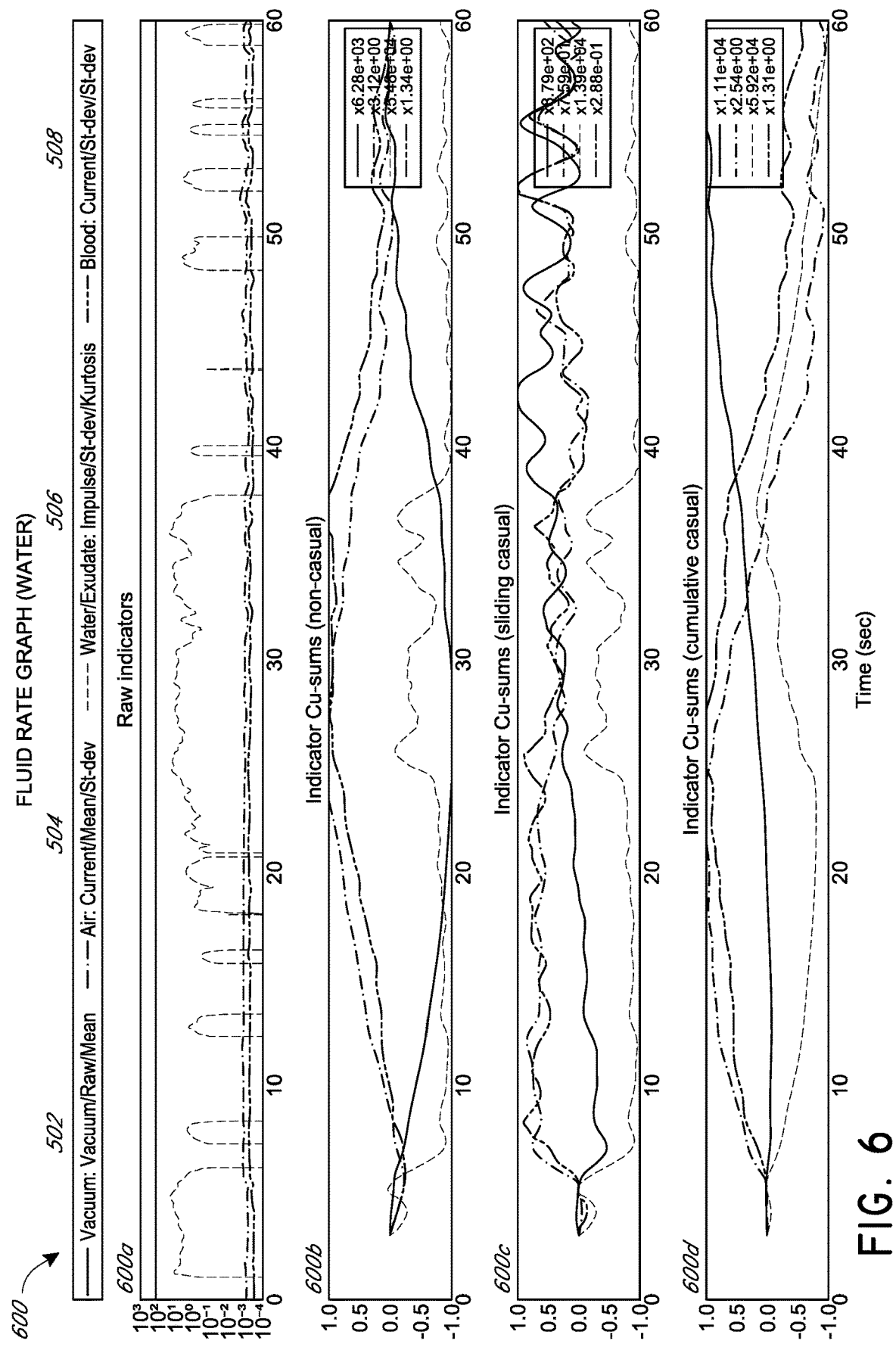
FIG. 6 illustrates detection of a change in fluid rate when water is being aspirated according to some embodiments.
Figure 7:
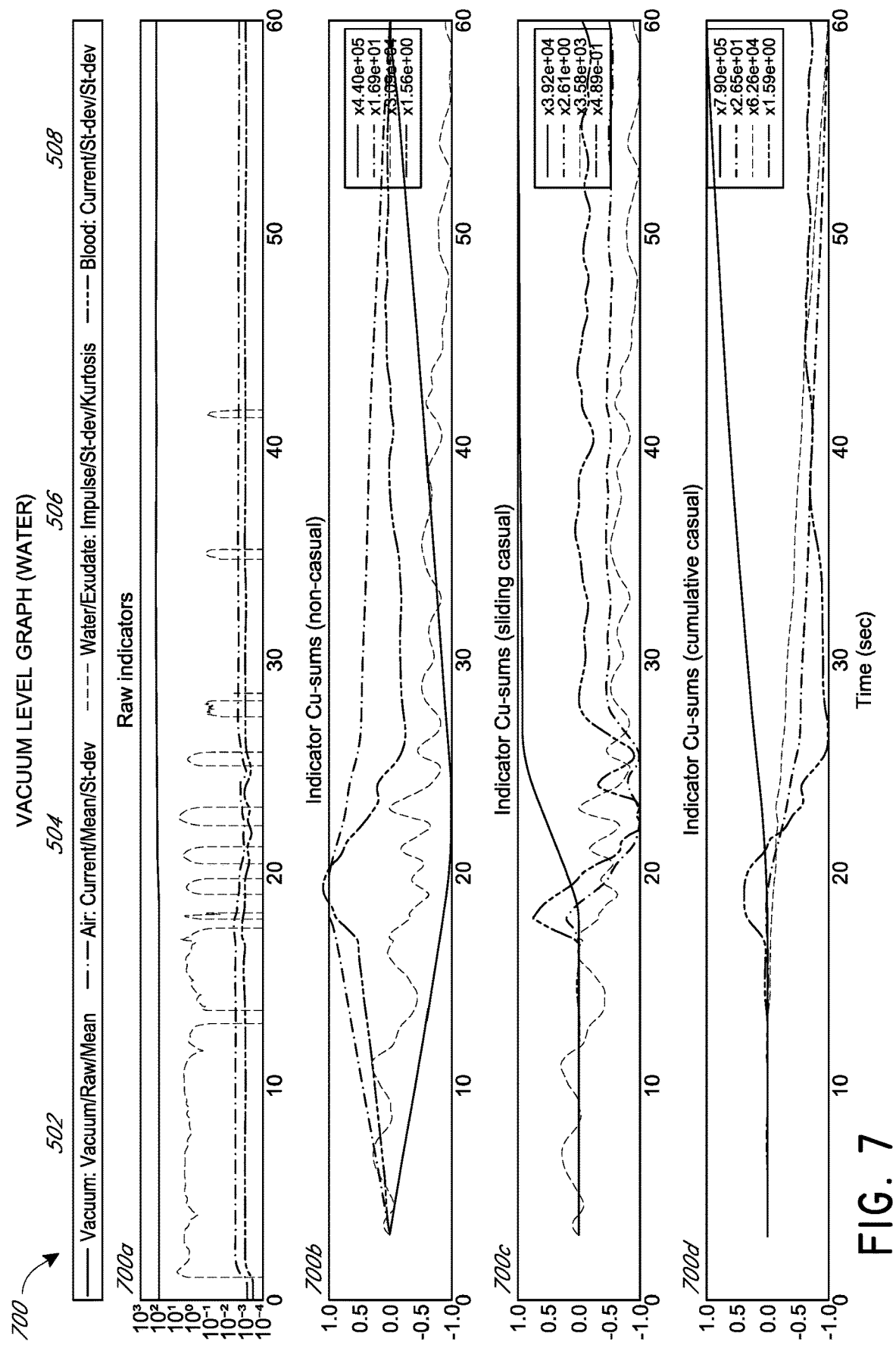
FIG. 7 illustrates detection of a change in vacuum level when water is being aspirated according to some embodiments.
Figure 8:
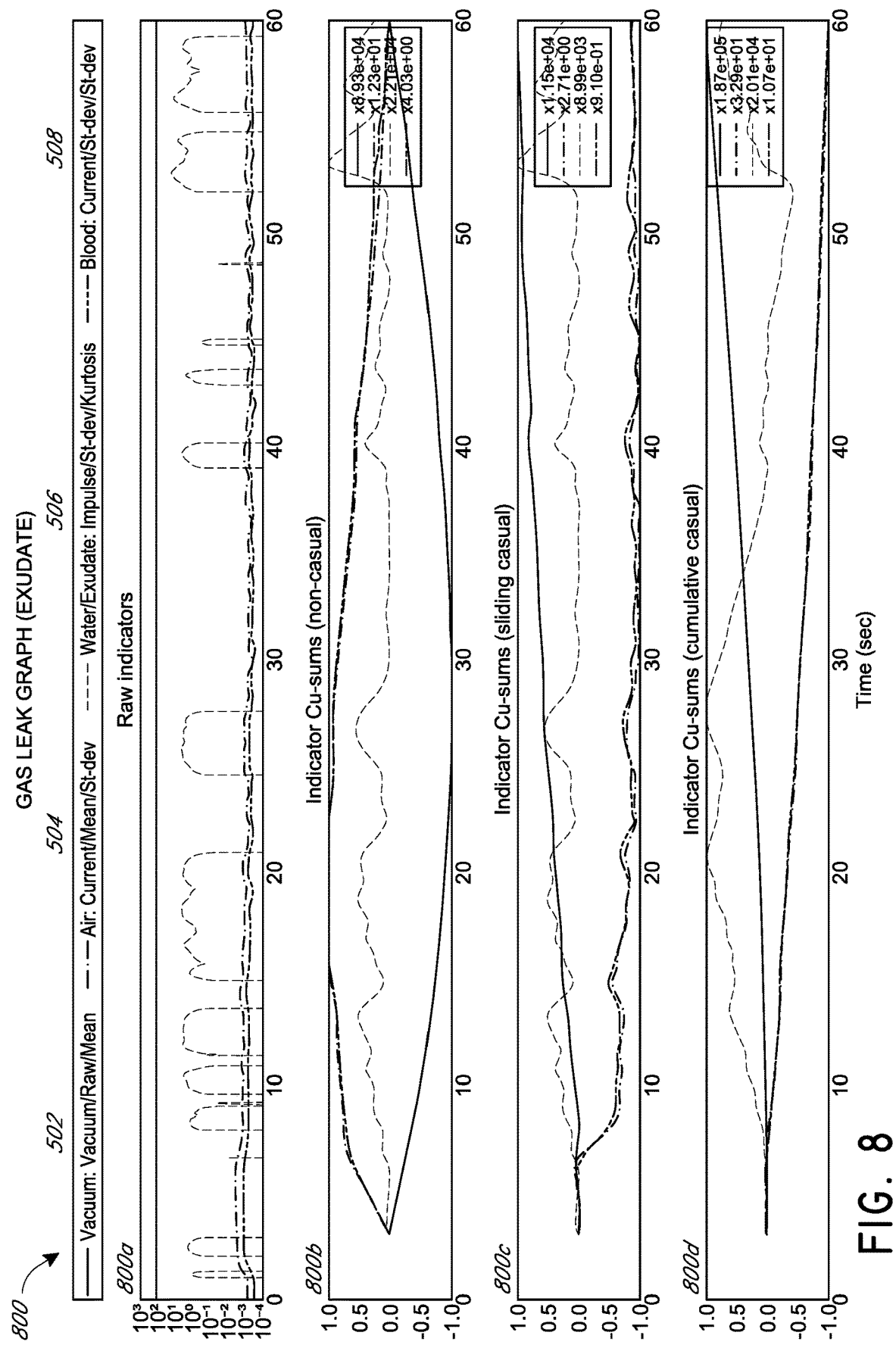
FIG. 8 illustrates detection of a gas leak when exudate is being aspirated according to some embodiments.
Figure 9:
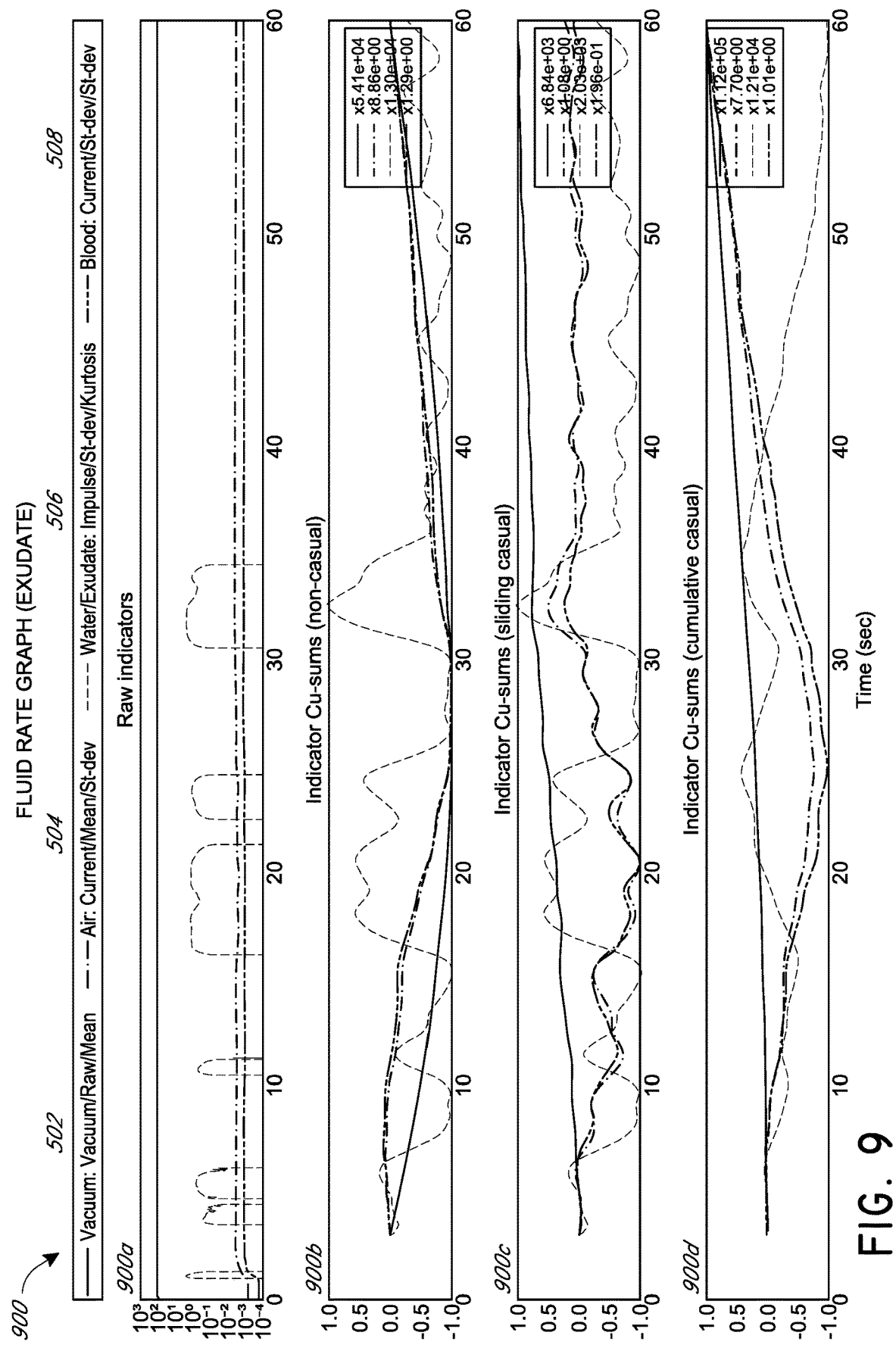
FIG. 9 illustrates detection of a change in fluid rate when exudate is being aspirated according to some embodiments.
Figure 10:
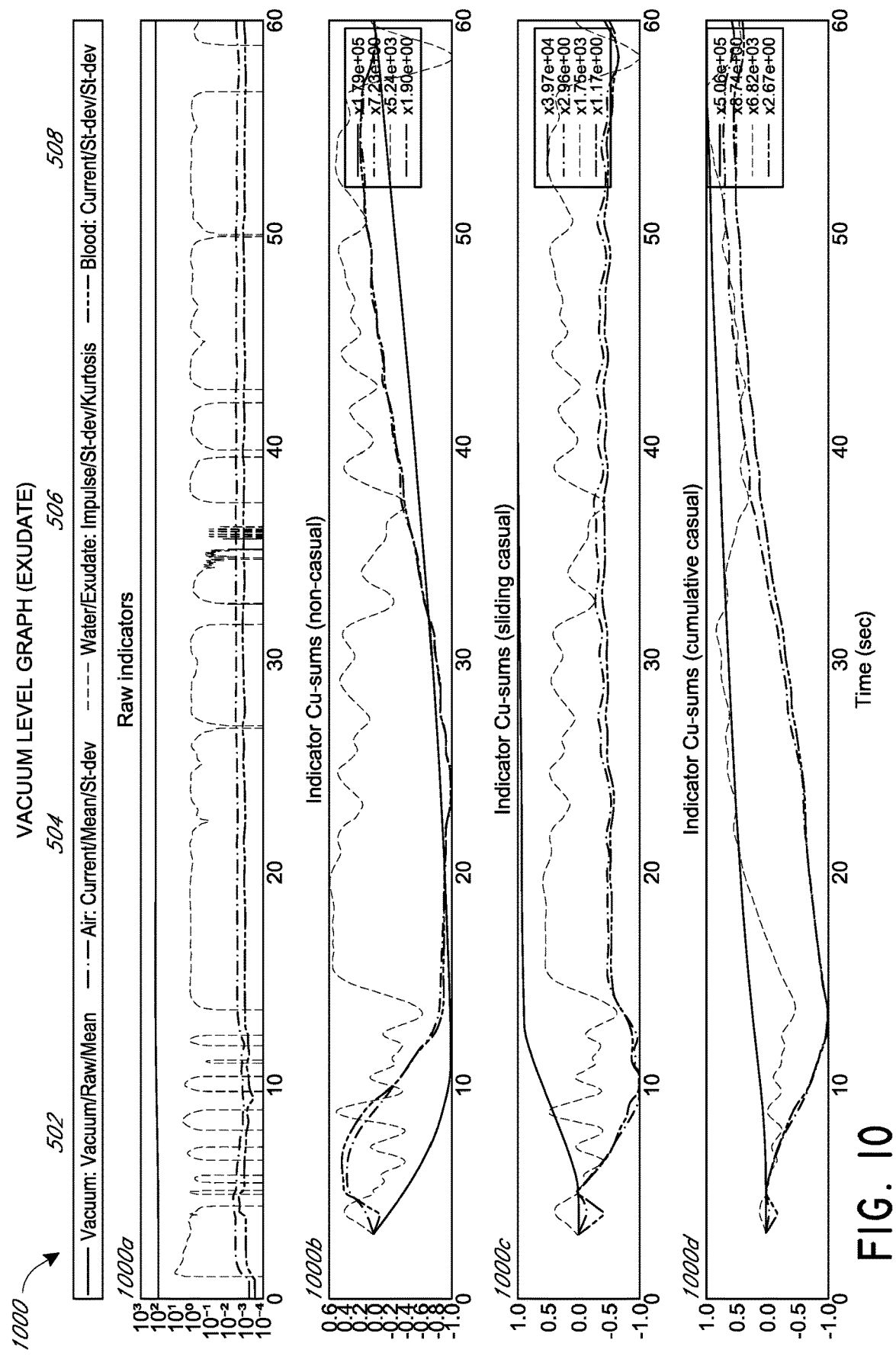
FIG. 10 illustrates detection of a change in vacuum level when exudate is being aspirated according to some embodiments.
Figure 11:
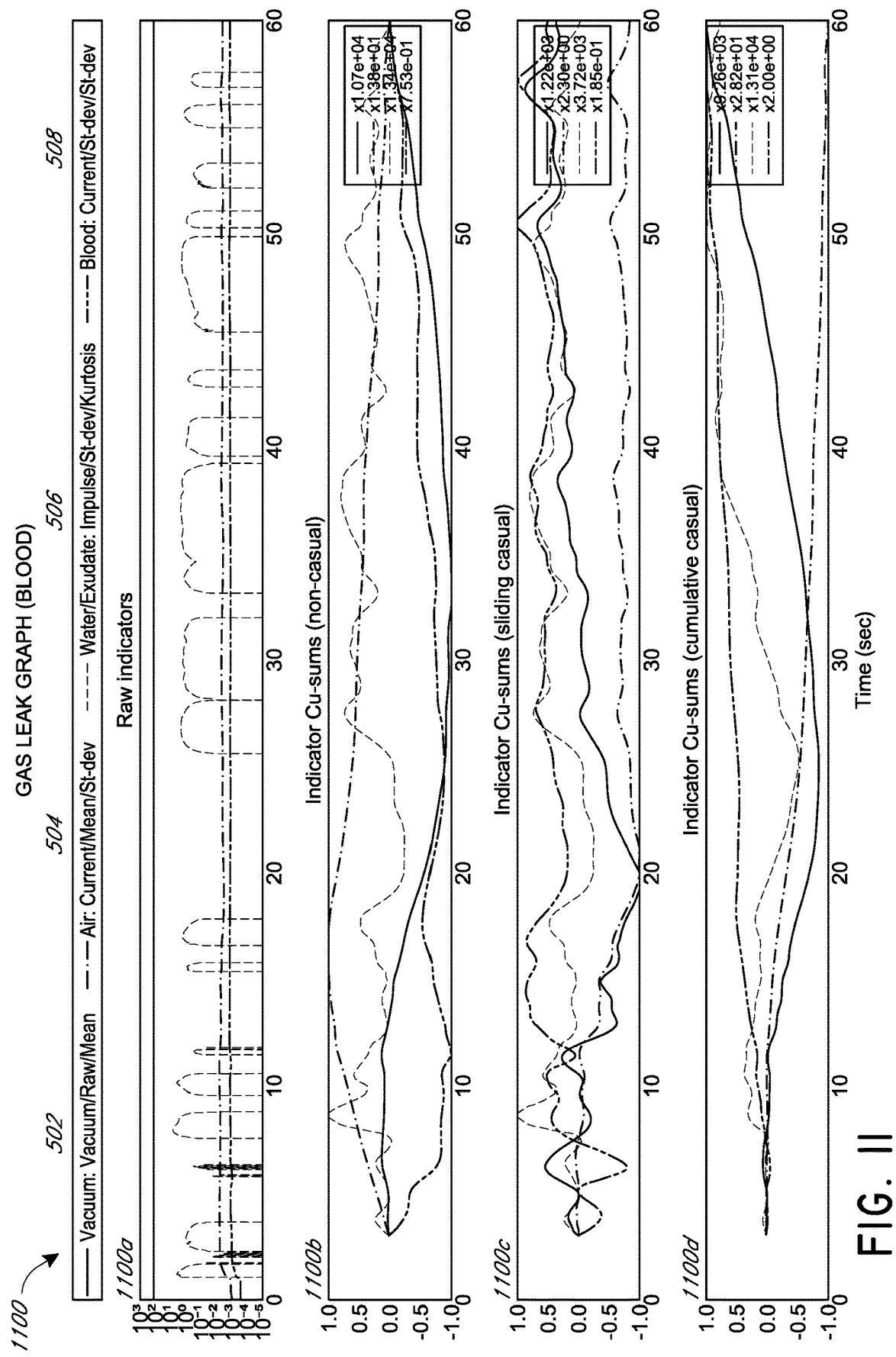
FIG. 11 illustrates detection of a gas leak when blood is being aspirated according to some embodiments.
Figure 12A:
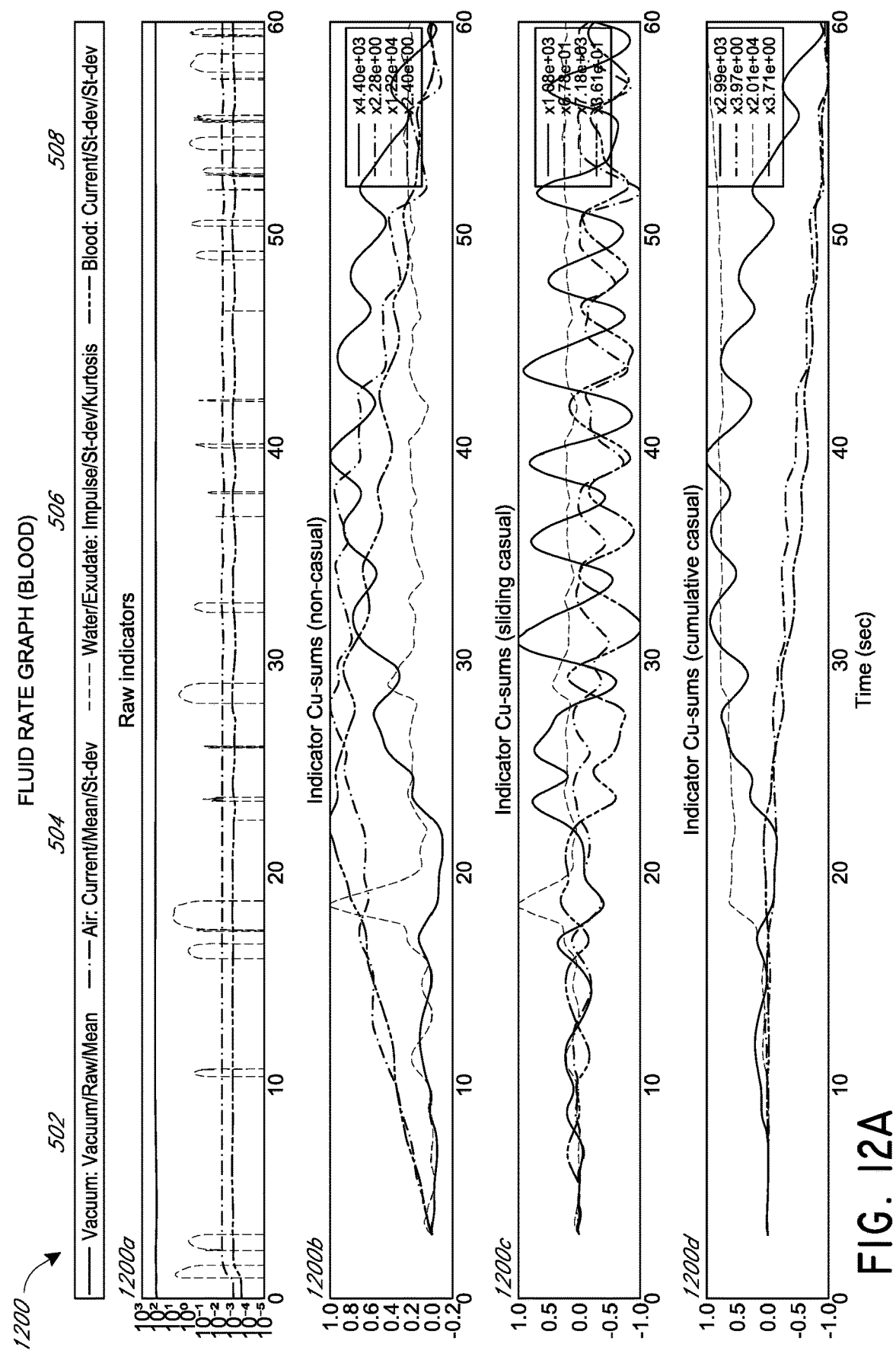
FIGS. 12A-B illustrate detection of a change in fluid rate when blood is being aspirated according to some embodiments.
Figure 12B:
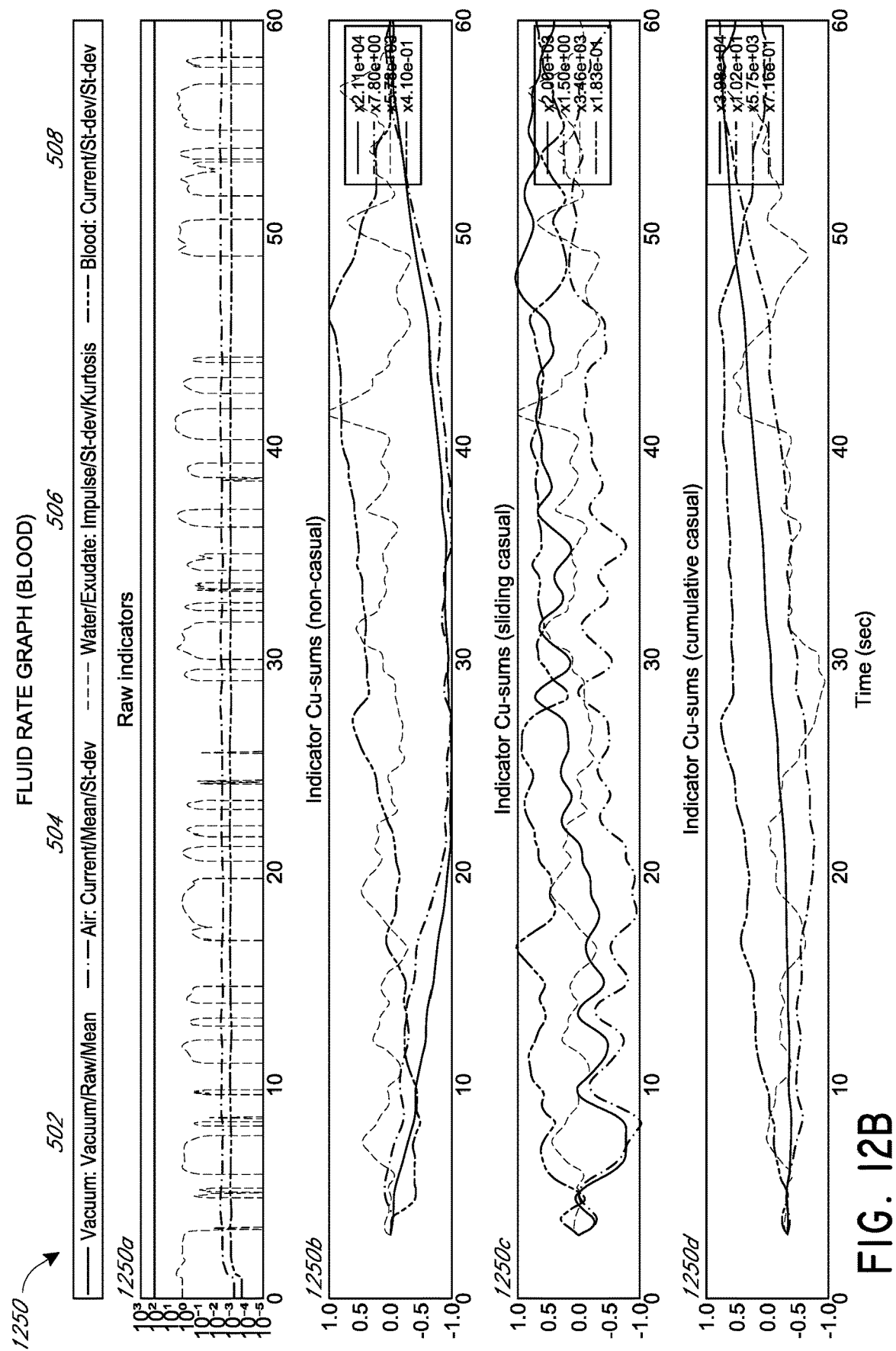
Figure 13:
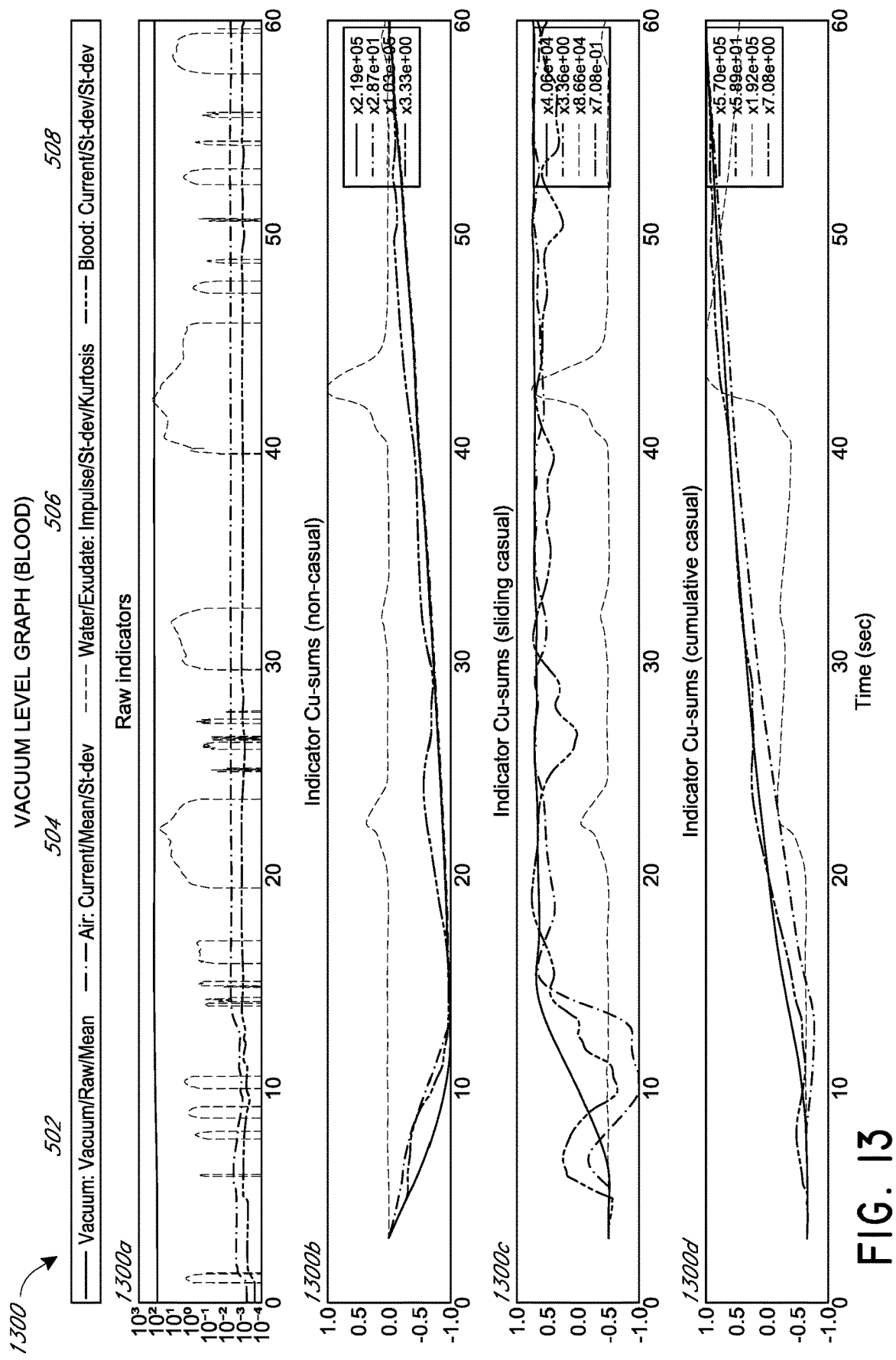
FIG. 13 illustrates detection of a change in vacuum level when blood is being aspirated according to some embodiments.

In some implementations, a negative pressure wound therapy system can include a negative pressure wound therapy device connected to a wound model and having one or more sensors to detect one or more of the signals in Table 1. The system can be operated under the conditions of changing one of vacuum level provided by the negative pressure source, rate of water removed from the wound, rate of exudate removed from the wound, rate of blood removed from the wound, or air leak rate in the fluid flow path while maintaining the other parameters constant. This way, operational parameters, such as those in FIG. 4, can be determined, statistics can be computed and analyzed (e.g., by using Cusum analysis), and the most appropriate statistic(s) for detecting and classifying operational conditions can be selected. For example, in the graphs illustrated in FIGS. 5-13, the system was operated initially in steady-state and thereafter one of the operational parameters or variables was changed. In FIGS. 5, 8, and 11, the intensity of gas (e.g., air) leak in the fluid flow path has been changed (e.g., from 60 sccm to 180 sccm at around 5 seconds) and collected and analyzed data is used to perform detection of an abrupt increase in the leak rate. In FIGS. 6 and 9, flow rate of fluid (water and exudate, respectively) has been changed (e.g., bolus of fluid introduced into the fluid flow path at around 5 seconds) and collected and analyzed data is used to perform detection of change in the fluid flow rate. In FIGS. 12A-B blood was introduced into the fluid flow path and collected and analyzed data is used to perform detection of blood. In FIGS. 7, 10, and 13, vacuum level produced by the negative pressure source has been changed (e.g., from −80 mmHg to −120 mmHg at around 18 seconds) and collected and analyzed data is used to perform detection of change in vacuum pressure in the fluid flow path.

In some embodiments, using correlation and fitness analysis described herein, the following statistics can be used to perform detection and classification:

TABLE 2

Statistics used for detection and classification

| Operational Condition | Statistic |
|---|---|
| Vacuum level | Mean of the raw vacuum (e.g., 502) |
| Gas leak rate | Standard deviation of the rolling mean of motor current (e.g., 504) |
| Water/Exudate rate | Kurtosis of the rolling standard deviation of pump speed (e.g., 506) |
| Blood rate | Standard deviation of the rolling standard deviation of the motor current (e.g., 508) |

FIGS. 5-13 illustrate plots of Cusum analysis of the statistics in Table 2 for detection and classification of various operational conditions. FIG. 5 illustrates detection 500 of a gas leak when water is being aspirated from a wound according to some embodiments. Four plots 500a, 500b, 500c, and 500d are illustrated corresponding to, respectively, raw (or unprocessed) values of the statistics in Table 2 and non-causal Cusum, sliding causal Cusum, and cumulative causal Cusum of the statistics in Table 2. In plots 500a-d, curves 502 represent raw and Cusum values of mean of raw vacuum, curves 504 represent raw and Cusum values of standard deviation of the rolling mean of motor current, curves 506 represent raw and Cusum values of kurtosis of rolling standard deviation of pump speed, and curves 508 represent standard deviation of rolling standard deviation of motor current. X-axes in the plots 500a-d corresponds to time duration (e.g., 60 seconds). Y-axis in plot 500a represents logarithmic scale (to normalized different raw values of the statistics), and y-axes in plots 500b-d are linearly scaled (or normalized) so that Cusum values are in the range (−1.0, 1.0). Plots 500a-d capture data corresponding to a change (e.g., increase) in the air leak rate (e.g., from 60 sccm to 180 sccm at around 5 seconds).

FIG. 6 illustrates detection 600 of a change in fluid rate when water is being aspirated from a wound according to some embodiments. Four plots 600a-d are illustrated corresponding to, respectively, raw (or unprocessed) values of the statistics in Table 2 (labeled 502, 504, 506, and 508) and non-causal Cusum, sliding causal Cusum, and cumulative causal Cusum of the statistics. Plots 600a-d capture data corresponding to a change (e.g., increase) in water flow rate due to bolus of water being released into the fluid flow path (e.g., at around 5 seconds).

FIG. 7 illustrates detection 700 of a change in vacuum level when water is being aspirated from a wound according to some embodiments. Four plots 700a-d, 600b, 600c, and 600d are illustrated corresponding to, respectively, raw (or unprocessed) values of the statistics in Table 2 (labeled 502, 504, 506, and 508) and non-causal Cusum, sliding causal Cusum, and cumulative causal Cusum of the statistics. Plots 700a-d capture data corresponding to a change (e.g., increase) in vacuum level provided by the pump (e.g., from −80 mmHg to −120 mmHg at around 18 seconds).

FIGS. 8, 9, and 10 correspond to FIGS. 5, 6, and 7 respectively except that exudate is being aspirated from a wound. FIGS. 8, 9, and 10 respectively illustrate detection 800, 900, and 1000 according to some embodiments.

FIG. 11 is similar to FIG. 5, but illustrates detection 1100 of a gas leak when blood is being aspirated from a wound according to some embodiments.

FIGS. 12A and 12B illustrate detection 1200 and 1250 of a change in fluid rate when blood is being aspirated from a wound according to some embodiments. Data in FIG. 12A has been collected in the presence of 60 sccm air leak. Data in FIG. 12B has been collected in the presence of 120 sccm air leak. FIGS. 12A-B are similar to FIG. 6. FIG. 13 is similar to FIG. 7, but illustrates detection 1300 of a change in vacuum level when blood is being aspirated according to some embodiments.

In some embodiments, travel of fluid (and rate of travel) through the fluid flow path from the wound bed toward the pump can be detected because of changes in the signals and statistics (Tables 1 and 2) due to changes in the flow path volume "seen" by the negative pressure source. For example, a slug of fluid travelling in the fluid flow path (e.g., between wound and canister) can slow down or prevent gas from flowing from behind it, thus causing the negative pressure source to have to remove less gas to maintain a target pressure (e.g., selected by a user or preset). The pressure differential in the fluid flow path (which can increase with increase in a gas leak rate) eventually pushes the slug closer to the negative pressure source, thus increasing the pressure between the negative pressure source and the slug (pressure is inversely proportional to volume in accordance with Boyle's Law). After the slug is aspirated into the canister, the negative pressure source then has to remove more gas left behind the slug to reach the target pressure. This variance in the activity or work rate of the negative pressure source will be further affected by the density or viscosity of the fluid (e.g., less dense water, more dense exudate, and even more dense blood) as these factors affect how slowly the slug will be pushed forward by the pressure differential in the flow path. For example, more viscous fluid will flow slower than less viscous fluid and changes in the volume seen by the negative pressure source (and associated pressure increases) can be smaller for more viscous fluid. Variance in the work rate can be captured via change(s) in PWM duty cycle, motor current, etc. In some instances, if an air leak develops (or increases in intensity), negative pressure in the fluid flow path will at least momentarily decrease. This may cause change(s) PWM duty cycle, motor current, etc. as the negative pressure source may have to work harder to maintain desired pressure.

As is illustrated in FIGS. 7, 10, and 13, according to some embodiments, a change in the vacuum level causes changes in each version of the Cusum for each variable that is the same or approximately the same order of magnitude or larger that the change in the vacuum level. This is particularly evident in the magnitude of the vacuum statistic 502 for sliding causal Cusum. The smallest vacuum step scale factor are all approximately $4.00 \times 10^{\wedge}4$. The largest non-vacuum step scaling factor is $1.15 \times 10^{\wedge}4$, and most are on the order of $10^{\wedge}3$. In some implementations, a threshold for detecting and classifying a vacuum change can be set at $3.00 \times 10^{\wedge}4$ or another suitable value.

As is illustrated in FIGS. 5, 6, 8, 9, 11, and 12A-B, according to some embodiments, the blood statistic (508) closely follows the gas (or air) leak statistic (504) for the exudate graphs (FIGS. 8 and 9) and water graphs (FIGS. 5 and 6), but is noticeably dissimilar for the blood graphs (FIGS. 11 and 12A-B).

Table 3 quantifies the similarity between the air and blood statistic plots according to some embodiments. Table rows have been ordered so that the vacuum level change graphs (regardless of fluid type) are at the top, followed by the change graphs involving blood, then change graphs involving exudate, and finally the change graphs involving water. The correlation coefficient between the air leak and blood statistics are calculated for the raw data and the three variants of the Cusum. The mean difference between the three variants of the Cusum (after they have been normalized to be in the range (−1.0, 1.0)) is also provided. Finally the means of the absolute differences for the normalized Cusums are provided.

Figure 14:
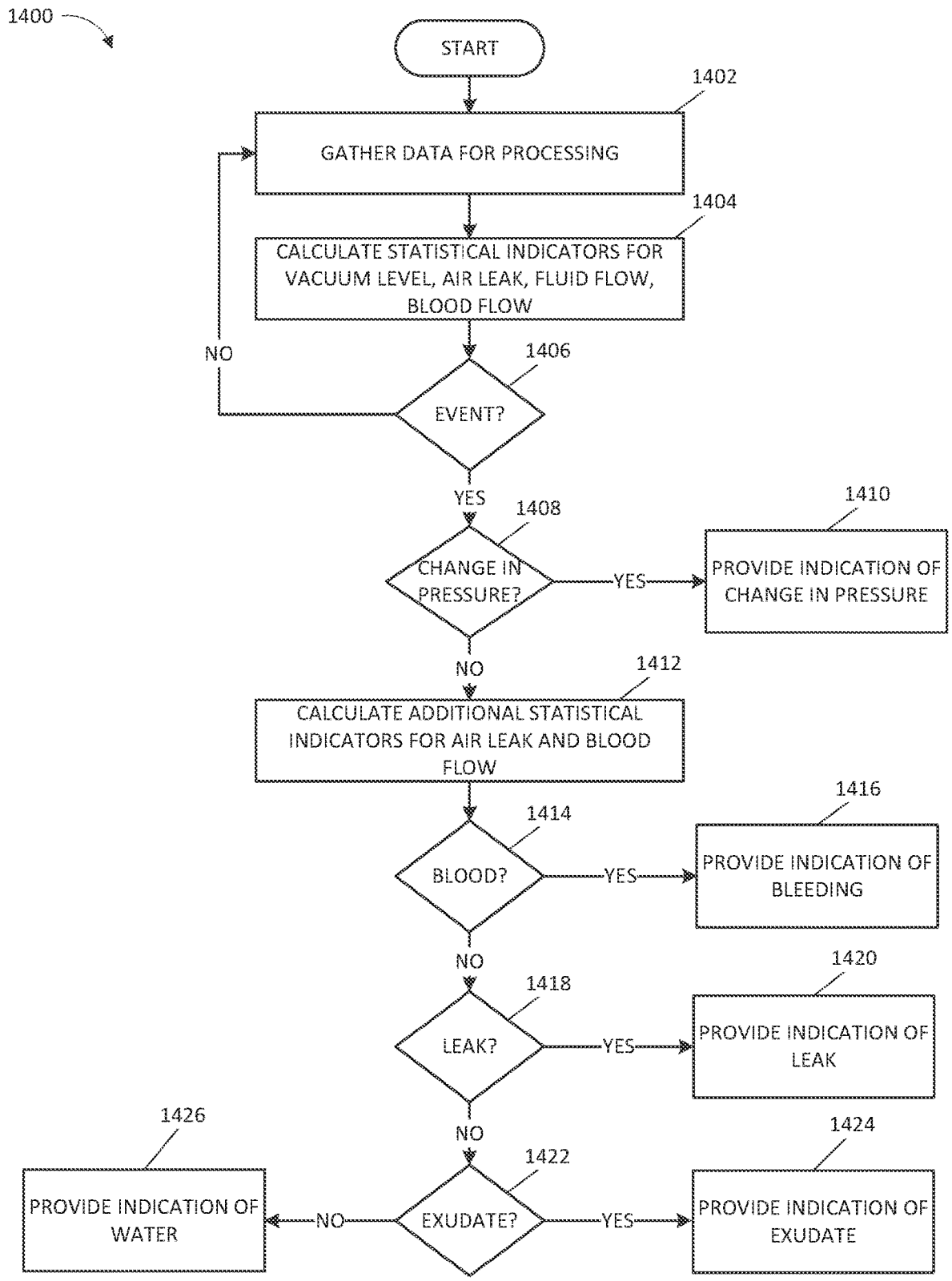
FIG. 14 illustrates a process for detecting and classifying operational conditions according to some embodiments.

With reference to the bold entries for the correlation coefficient of the sliding Cusum, and the mean absolute difference of the sliding Cusum in Table 3, the blood graphs can be clearly separated from the non-blood graphs. In some embodiments, a threshold of 0.65 or another suitable value will delineate blood from non-blood for the correlation coefficient (e.g., if blood is detected, the correlation coefficient will be smaller than 0.65). A threshold of 0.2 or another suitable value can perform the superstation of the normalized sum of absolute difference (e.g., if blood is detected, the normalized sum of absolute difference will be greater than 0.2). The raw values, non-causal Cusum, and cumulative causal Cusum may not provide this separation. For this reason, the sliding causal Cusum algorithm can be used for the thresholds for detection and classification of an event, vacuum level, gas leak, and exudate/water differentiation as illustrated in FIG. 14. This may advantageously allow a single version of Cusum to be used.

Once the vacuum level step graphs have been eliminated a leak indicator can be used to detect changes in air leaks, such as abrupt changes according to some embodiments. As is illustrated in FIGS. 5, 6, 8, 9, 11, and 12A-B, the sliding causal Cusum for the air leak statistic (504) is consistently below −2.0 (when taking the scale factor into account) when air leak changes occur, and above −2.0 otherwise. This may be so whether or not the changes with blood are considered. In some implementations, the threshold used for fluid detection is −2.0 or another suitable number.

In some embodiments, exudate and water can be differentiated if desired using the water/exudate statistic (506) once all the vacuum level changes, air leak rate changes, blood detection have been accounted for. It can be seen that the exudate rate step graph has a limit of $-2.0 \times 10^{\wedge}3$ and the water step graph a limit of $-1.4 \times 10^{\wedge}4$. A threshold of $-1.0 \times 10^{\wedge}4$ or another suitable value can be used to differentiate between exudate and water.

In some embodiments, it may be advantageous to discern whether an event (change in operation) has taken place in the first place. This can be reliably determined from examining the vacuum statistics (502) sliding Cusum. Taking into account that the vacuum level produced by the negative pressure source is controlled, any significant deviation may be indicative of an external disturbance. This observation is corroborated by the constant value of the sliding causal Cusum of the vacuum metric (502) prior to the change taking place in FIGS. 5-7, 9, and 13. FIG. 6 has the smallest scale factor (879) for the vacuum statistic (502) sliding causal Cusum plots (600c). In some implementations, 500 or another suitable value can be used as a threshold for event detection before event classification is attempted.

Although some embodiments describe detection of increases in fluid flow rates, gas leak rate, vacuum pressure level, and the like, systems and methods described herein can be used to detect decreases in one or more operational conditions.

TABLE 3

Similarity measures between air leak and blood data

| Graph type | | Associated FIG. | Raw data, correlation coefficient | Non-causal Cusum, correlation coefficient | Sliding causal Cusum, correlation coefficient | Cumulative causal Cusum, correlation coefficient | Non-causal Cusum, mean normalized differences | Sliding causal Cusum, mean normalized differences |
|---|---|---|---|---|---|---|---|---|
| Vacuum level | blood | FIG. 13 | 0.812 | 0.94 | 0.801 | 0.987 | −0.082 | 0.007 |
| Vacuum level | exudate | FIG. 10 | 0.896 | 0.997 | 0.976 | 0.998 | 0.003 | 0.066 |
| Vacuum level | water | FIG. 7 | 0.759 | 0.721 | 0.77 | 0.85 | 0.276 | −0.29 |
| Air leak | blood | FIG. 11 | 0.338 | −0.762 | −0.385 | −0.956 | 1.023 | −1.058 |
| Fluid rate | blood | FIG. 12A | 0.671 | 0.861 | 0.463 | 0.961 | 0.064 | 0.098 |
| Fluid rate | blood | FIG. 12B | 0.689 | −0.7 | −0.441 | −0.158 | −0.78 | −0.915 |
| Air leak | exudate | FIG. 8 | 0.974 | 0.997 | 0.99 | 1 | −0.017 | −0.037 |
| Fluid rate | exudate | FIG. 9 | 0.929 | 0.996 | 0.98 | 0.994 | −0.008 | 0.026 |
| Air leak | water | FIG. 5 | 0.968 | 0.993 | 0.986 | 0.999 | −0.038 | −0.036 |
| Fluid rate | water | FIG. 6 | 0.779 | 0.87 | 0.832 | 0.915 | −0.035 | −0.017 |

| Graph type | | Cumulative causal Cusum, mean normalized differences | Non-causal Cusum, mean normalized absolute differences | Sliding causal Cusum, mean normalized absolute differences | Cumulative causal Cusum, mean normalized absolute differences |
|---|---|---|---|---|---|
| Vacuum level | blood | −0.095 | 0.109 | 0.198 | 0.096 |
| Vacuum level | exudate | 0.091 | 0.025 | 0.076 | 0.095 |
| Vacuum level | water | −0.023 | 0.276 | 0.292 | 0.168 |
| Air leak | blood | −1.123 | 1.023 | 1.111 | 1.127 |
| Fluid rate | blood | 0.046 | 0.128 | 0.262 | 0.086 |
| Fluid rate | blood | −0.528 | 0.872 | 0.916 | 0.674 |
| Air leak | exudate | −0.017 | 0.025 | 0.045 | 0.017 |
| Fluid rate | exudate | 0.088 | 0.026 | 0.069 | 0.091 |
| Air leak | water | −0.022 | 0.043 | 0.041 | 0.023 |
| Fluid rate | water | −0.218 | 0.168 | 0.132 | 0.329 |

FIG. 14 illustrates a process 1400 for detecting and classifying operational conditions according to some embodiments. The process 1400 can be implemented by any pump assembly described herein, such as by any one or more of the processors described herein. The process 1400 can be used to detect occurrence of an event and classify the event as one of: vacuum level change, blood detected, air leak change (e.g., sudden or abrupt) detected, exudate detected, or water detected. In some embodiments, the process 1400 can alternatively or additional provide magnitude or another parameter associated with the event, such as new vacuum level, blood flow rate, air leak rate, exudate flow rate, or water flow rate.

In block 1402 the process 1400 collects data, such as data for signals in Table 1. Data can be collected over one or more analysis windows (e.g., 60 second windows or any other suitable period of time). The process 1400 can transition to block 1404 where it determines sliding causal Cusum for statistics, such as statistics in Table 2. The process 1400 can transition to block 1406 where it detects occurrence of an event. As is described herein, the process 1400 can determine if the sliding causal Cusum of the vacuum level exceeds a threshold (e.g., absolute maximum Cusum value exceeds 500 or another suitable value). If the sliding causal Cusum of the vacuum level does not exceed the threshold, the process 1400 returns to block 1402. On the other hand, if the sliding causal Cusum of the vacuum level satisfies the threshold, an event has occurred and the process 1400 can transition to block 1408 to classify the event.

In block 1408, the process 1400 determines if change in pressure level has been detected. As is described herein, the process 1400 can determine if the sliding causal Cusum of the vacuum level exceeds a threshold (e.g., absolute maximum Cusum value exceeds 3.00×10^4 or another suitable value). If the sliding causal Cusum of the vacuum level exceeds the threshold, the process 1400 transitions to block 1410 where it can provide indication that change in pressure has been detected. Indication can include one or more of audio, visual, tactile indications (e.g., alarms) as described herein. Indication can also include adjusting operation of the negative pressure source, such as one or more of increasing negative pressure, decreasing negative pressure, or stopping delivery of negative pressure. Indication can include providing an alarm.

If the sliding causal Cusum of the vacuum level does not satisfy the threshold in block 1408, the process 1400 can transition to block 1412 to continue classification. In block 1412, the process 1400 can compute correlation coefficient of air leak statistic or indicator (504) sliding causal Cusum and blood statistic or indicator sliding causal Cusum (508) as described herein. In some implementations, alternative or additional correlation coefficients may be computed, such as a correlation coefficient of fluid rate statistic or indicator (506) sliding causal Cusum and blood indicator sliding causal Cusum (508).

The process 1400 can transition to block 1414 where it determines if blood has been detected. The process 1400 can compare the correlation coefficient computed in block 1414 to a threshold (e.g., 0.65 or another suitable value). If the correlation coefficient is below the threshold, the process 1400 transitions to block 1416 where it can provide indication (e.g., high priority alarm) that blood has been detected in the fluid flow path. The indication can be provided using any of the approaches described herein and may also be transmitted to a remote monitoring station using any of communication techniques described herein. In some embodiments, the process 1400 can adjust operation of the negative pressure source, such as by one or more of: maintain or decrease the negative pressure level provided by the negative pressure source (for example, decrease negative pressure progressively if blood detection persists over a time period), stop delivery of negative pressure (e.g., immediately or after a period of time during which negative pressure level is decreased or not increased), or vent negative pressure to atmosphere (e.g., by opening one or more valve(s) positioned in the flow path) to prevent further bleeding.

If the correlation coefficient does not satisfy the threshold in block 1414, the process 1400 transitions to block 1418 where it determines if a leak has been detected. The process 1400 can compare the sliding causal Cusum of the air leak statistic or indicator to a threshold (e.g., absolute minimum Cusum falls below −2.0 or another suitable threshold). If the sliding causal Cusum is below the threshold, the process 1400 can transition to block 1420 where it can provide indication that a leak has been detected. The indication can be provided using any of the approaches described herein and may include indicating the detected leak rate.

If the sliding causal Cusum of the air leak indicator does not satisfy the threshold in block 1418, the process 1400 transitions to block 1422 to determine presence of exudate or water. The process 1400 can compare the fluid rate statistic (506) sliding causal Cusum to a threshold (e.g., compare the minimum of sliding causal Cusum to $-1.0 \times 10^{4}$ or another suitable value). If the sliding causal Cusum is below the threshold, the process 1400 can transition to block 1424 where it can provide indication that exudate has been detected. Otherwise, the process can transition to block 1426 where it can provide indication that water has been detected. The indication in blocks 1424 and 1426 can be provided using any of the approaches described herein.

Additional or alternative statistics can be used for detection of one or more operational conditions. In some embodiments, one or more of the following statistics can be used to detect change in vacuum pressure (listed in the order of highest to lowest distinctiveness):
 1 mean of peak to peak (P2P) of current signal
 2 minimum of standard deviation (StD) of current signal
 3 mean of StD of current signal
 4 mean of vacuum signal
 5 mean of mean of vacuum signal
 6 StD of current signal
 7 minimum of P2P of current signal
 8 maximum of vacuum signal
 9 maximum of mean of vacuum signal
 10 maximum of StD of current signal
 11 maximum of mean of current signal
 12 mean of mean of current signal
 13 mean of current signal
 14 maximum of current signal
 15 maximum of P2P of current signal
 16 minimum of mean of vacuum signal
 17 minimum of vacuum signal
 18 minimum of mean of current signal
 19 kurtosis of PWM signal In certain embodiments, using any one or more of input signals not directly associated with the pressure measurement, such as mean of peak to peak (P2P) of current signal, can advantageously provide for redundancy and additional system safety in case of partial or full malfunction of the pressure sensor. In certain implementations, pressure levels measured indirectly can be used to supplement direct readings by the pressure sensor. This can improve accuracy, reduce system cost (e.g., by allowing cheaper, less accurate pressure sensor to be used), etc. The system could also detect malfunction of the pressure sensor, which can assist with troubleshooting and repair. In some cases, any one or more of these advantages can be realized by using pressure data measured by the pressure sensor instead of or in addition to negative pressure source activity data described in the following paragraphs to indirectly measure pump activity.

In some implementations, one or more of the following statistics can be used to detect change in gas leak rate (listed in the order of highest to lowest distinctiveness):
 1 StD of mean of current signal
 2 minimum motor speed signal
 3 mean of P2P of vacuum signal
 4 mean of StD of vacuum signal
 5 StD of vacuum signal
 6 StD of mean of vacuum signal
 7 skewness of P2P of vacuum signal
 8 minimum of mean motor speed signal
 9 skewness of StD of vacuum signal
 10 StD of P2P of vacuum signal In certain embodiments, one or more of the following statistics can be used to detect change in fluid rate (listed in the order of highest to lowest distinctiveness):
 1 kurtosis of StD of motor speed signal
 2 kurtosis of StD of PWM signal
 3 kurtosis of mean of PWM signal
 4 StD of mean of PWM signal In certain implementations, one or more of the following statistics can be used to detect change in water rate (listed in the order of highest to lowest distinctiveness):
 1 kurtosis of StD of pump speed signal
 2 kurtosis of mean of pump speed signal In some embodiments, one or more of the following statistics can be used to detect change in exudate rate (listed in the order of highest to lowest distinctiveness):
 1 kurtosis of StD of pump speed signal
 2 kurtosis of StD of PWM signal
 3 kurtosis of mean of pump speed signal In some implementations, one or more of the following statistics can be used to detect blood (listed in the order of highest to lowest distinctiveness):
 1 StD of StD of current signal
 2 kurtosis of vacuum signal
 3 kurtosis of mean of vacuum signal In some instances, in addition to or as an alternative to expert system detection and classification illustrated in FIG. 14, artificial intelligence classifiers, such as neural networks, Naïve Bayes classifiers, and support vector machines, can also be used to detect and classify one or more operational conditions.

Low Pass Filter Detection and Classification

Figure 15A:
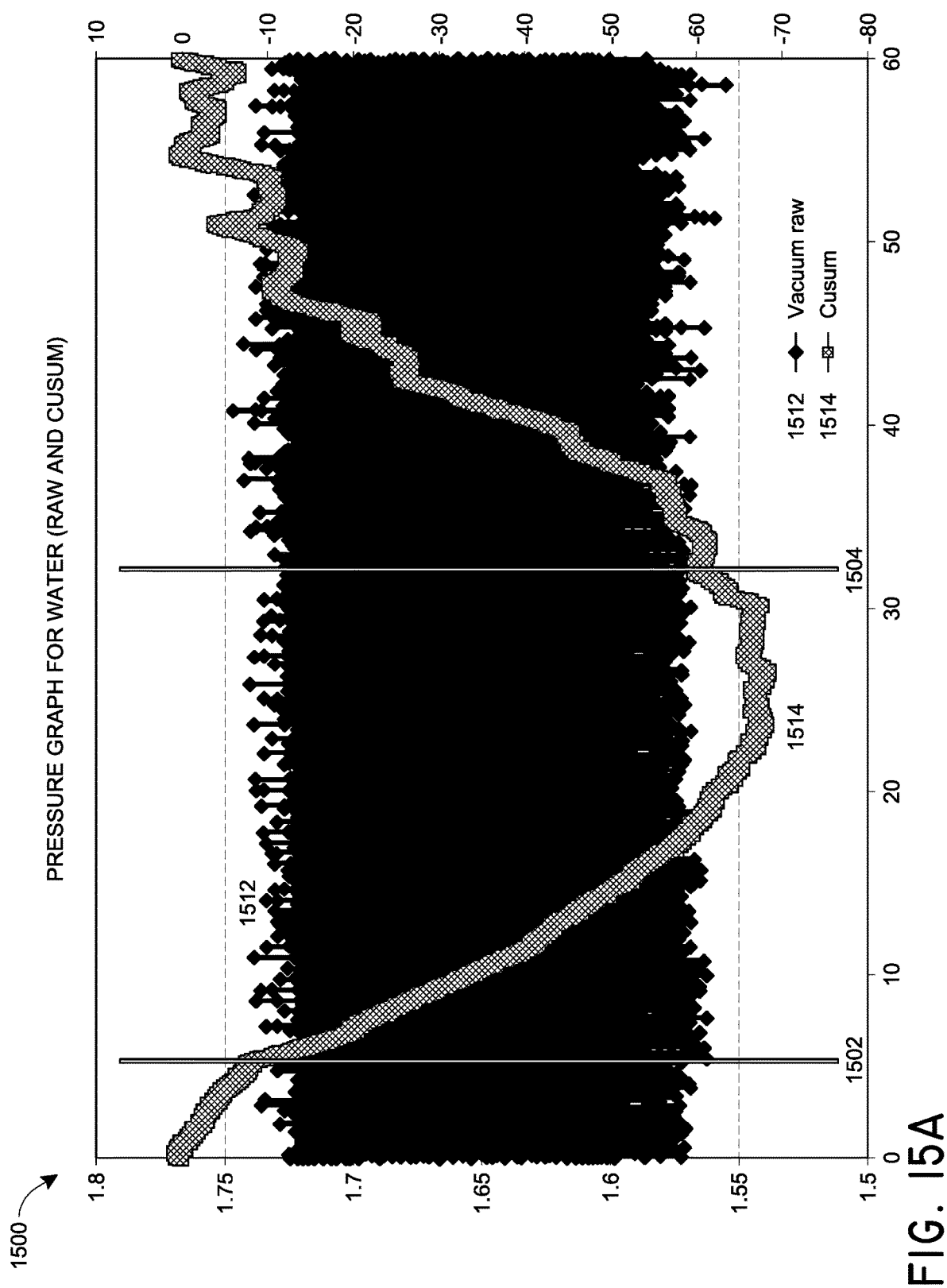

In some embodiments, low pass filter analysis can be used in addition to or instead of time domain analysis for detection and classification of one or more operational conditions. FIGS. 15A-B illustrate vacuum pressure data graphs when water is being aspirated according to some embodiments. FIG. 15A illustrates a graph 1500 that depicts sensed pressure values 1512 (having magnitudes indicated by right y-axis) and Cusum of pressure values 1514 (having magnitudes indicated by left y-axis) over a 60 second time duration. FIG. 15B illustrates a graph 1550 that illustrates only the pressure values 1514.

At around 5 seconds (indicated by line 1502) a bolus of water was released into the wound model. At around 33 seconds (indicated by line 1504) water slugs started to enter the canister. As is shown in FIG. 15A and explained herein, Cusum of pressure values 1514 tracks the changes in pressure in the flow path and can be used to detect presence of water or water flow rate.

In some embodiments, pressure values 1514 can be analyzed using a low pass filter to alternatively or additionally detect presence of water or water flow rate. Referring to FIG. 15B, it can be observed that the number of pressure samples that have magnitudes greater than a measure of average maximum peak value (illustrated by line 1520) or another suitable indicator that tracks the envelope of the pressure signal increases to the right of line 1504 (or after fluid slugs start entering the canister). One such cluster of "outlier" pressure samples exceeding (or being less negative) in magnitude than the threshold corresponding to line 1520 is illustrated in the interval 1530. This increase in the number of pressure sample "outliers" may be due to transient changes in the volume (for example, decrease) seen by the negative pressure source as fluid slugs are being aspirated into the canister, which can cause a correspondingly proportional change (for example, decrease) in the negative pressure. Detecting and counting such outliers can be used to detect presence of water or water flow rate.

In some implementations, outliers on the bottom side of the pressure graph 1550 can be used additionally or alternatively, and a measure similar to line 1520 can be used as a threshold. These outliers will be detected as having pressure magnitude that is less (or is more negative) than the threshold. In some cases, outliers can be detected earlier in time than after line 1504, such as after line 1502 when water bolus starts to fill the dressing.

In certain implementations, detection of water can be performed as follows. Pressure signal samples can be collected over at least one time window (e.g., of 60 second duration or another suitable duration). The number and duration of windows can depend on the level of activity of negative pressure source (e.g., pump speed). Mean of pressure signal samples in the at least one window can be determined and outliers are identified based on amplitude deviation or variance from the mean satisfying a threshold. The mean can be determined using a low pass filter, by averaging, etc. When a number of outliers detected in the at least one window (or portion of the at least one window) has been detected, indication can be provided using any of the techniques described herein.

In some implementations, envelope detection of the pressure signal can be performed in addition to or alternatively to approaches described herein. The signal envelope can provide information about the number or magnitude of outliers based on, for example, changes in the slope (e.g., first derivative) of the envelope signal. Envelope detection can be synchronized to negative pressure source activity, such as to motor speed to improve detection accuracy. Envelope detection can be performed in software/firmware or hardware. For example, envelope detector circuit can be used, which in its simplest form can include a diode connected to a capacitor and resistor placed in parallel, with the envelope (output) being measured across the resistor. In certain cases, the output of the pressure sensor can be connected as input to the envelope detector circuit (e.g., connected to the diode), and detection can be performed on analog signals without digitizing the signals. As another example, envelope detection can be performed using a precision rectifier connected to a low pass filter.

In some embodiments, detection of operational conditions other than water can be performed using similar approach, such as detection of blood, exudate, gas leak, or vacuum level change. These operational conditions can be classified or distinguished. In some implementations, detector output can be used to modulate pump motor speed (e.g., by controlling the PWM signal). For example, if blood flow rate is being detected, pump motor can be controlled based on an inverse relationship to the blood flow rate (e.g., pump motor can be slowed down to decrease the negative pressure level in response to detection of increase in the blood flow rate). In certain implementations, detector output can be used to drive an indicator, such as an indicator light, to provide direct feedback to a user.

In some embodiments, detection and classification using low pass filter analysis (or time domain analysis) can be performed using a dedicated co-processor or digital signal processor. This can offload one or more of the central processor or pump control processor and improve performance of the system.

In some embodiments, presence or flow rate of additional or alternative fluids other than blood, exudate, and water can be detected using any of the approaches described herein.

Other Variations

Figure 16:
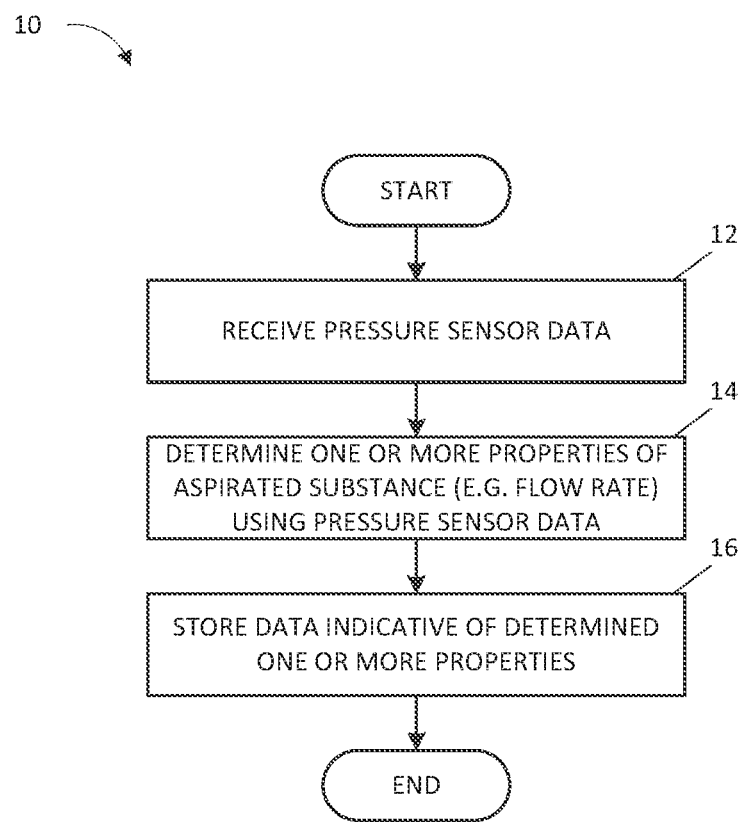
FIG. 16 illustrates a process for detection of a fluid according to some embodiments.

FIG. 16 illustrates a flow estimation process 10 performable by a device, such as the pump assembly 150 of FIG. 1, the pump assembly 230 of FIG. 2, or other pump assemblies described herein. In some embodiments, the process 10 can be implemented by one or more of the processors described herein. For convenience, the flow estimation process 10 is described in the context of system 100 of FIG. 1, but may instead be implemented in other systems described herein or by other computing systems not shown.

The flow estimation process 10 can enable the pump assembly 150 to determine an estimated composition of a substance in the fluid flow path so that the pump assembly 150 can differentiate between various substances (e.g., blood versus liquid or gaseous exudate) in the fluid flow path. For example, the pump assembly 150 can advantageously, in certain embodiments, output an indication of presence of blood in the fluid flow path (such as in the dressing, the tube 140, or in the canister (if present)) for display to a user of the pump assembly 150 or adjust an operation of the pump assembly 150, such as an operation of a source of negative pressure of the pump assembly 150 (e.g., pause operation of the source of negative pressure), in view of detecting the presence of blood in the flow fluid path.

At block 12, the process 10 can receive the pressure sensor data indicative of a measured pressure in the fluid flow path, which includes the tube 140. The pressure can be measured, for instance, by one or more of the pressure sensors described herein. The one or more pressure sensors can communicate information via a wire or wirelessly. In certain implementations, one of the pressure sensors can be positioned at or near the wound and wirelessly communicate information to the pump assembly 150. In some embodiments, pressure sensor data includes multiple pressure values taken over a duration of time, such as 1 microsecond or less, 1 millisecond, 0.5 seconds, 1 second, 3 seconds or more, and the like.

At block 14, the process 10 can determine one or more properties of a substance in the fluid flow path using the pressure sensor data. For example, the processor can examine a rate of change of pressure (e.g., in peak-to-peak pressure or maximum pressure) in the fluid flow path using the pressure sensor data to determine changes in the flow. The measured pressure can, for instance, be relatively higher when blood or tissue clots enter or flow in the fluid flow path than when liquid or gaseous exudate enters or flows in the fluid flow path, and thus the rate of change of the pressure can indicate presence of blood or tissue clots in the fluid flow path. Because blood or tissues clots have higher density than liquid or gaseous exudate, the rate of flow decreases and the fluid flow path volume "seen" by the source of negative pressure (e.g., combined volume of the tube 140, the canister (if present), and wound dressing downstream of the source of negative pressure) is reduced when blood or tissue clots are aspirated into the fluid flow path. This reduction in volume can cause an increase (e.g., spike) in the sensed pressure signal. Such increase can have one or more characteristics indicative of the change in the flow (e.g., reduction in flow due to the presence of blood or tissue clots) of the aspirated material. For example, blood or tissue clots being aspirated into and moving through the fluid flow path, may be interspersed with pockets of liquid or gaseous exudate moving through the fluid flow path. Because liquid or gaseous exudate is less dense, it will flow more rapidly than blood or tissue clots. These changes in flow will be reflected in the sensed pressure signal as follows: during movement of denser material through the fluid flow path, the pressure signal will increase, whereas during movement of less dense material (e.g., liquid or gaseous exudate) through the fluid flow path, the pressure signal will decrease. This pattern of increased pressure followed by decreased pressure (or vice versa) can be indicative of the presence of blood or tissue clots in the fluid flow path. For example, one or more of the duration of time between pressure increases and decreases (or vice versa), actual values of increased and decreased pressure, and the like can be compared to one or more of a set of thresholds to determine whether blood or tissue clots are being aspirated into the fluid flow path.

The multiple pressure sensor values collected over a period of time can be used to determine presence of blood. For example, the rate of change of the pressure can be analyzed over the period of time by comparing the multiple determined rates of changes to one or more thresholds. If the one or more thresholds is satisfied N times (where N is an integer, such as two, three, four, or more) over the period of time, the processor can indicate that blood has been detected. Advantageously, in certain embodiments, this approach can prevent false positives due to errant pressure readings, noise, and the like.

The processor can be a processor dedicated to processing pressure sensor data from one or more of the pressure sensors and outputting one or more signals based thereon (e.g., the processor can be coupled to or mounted on the one or more pressure sensors, can be a dedicated digital signal processor (DSP), etc.), or the processor can additionally process other non-pressure sensor data and output one or more signals based thereon for the pump assembly 150.

At block 16, the processor of the pump assembly 150 can store in a memory device the determined one or more properties (such as the estimated flow rate), for instance, for later reference or outputting.

In some implementations, at least two pressure sensors can be positioned in the fluid flow path to permit differential measurement of the pressure, which can be used in addition to or instead of the rate of change to determine presence of blood. For example, a first pressure sensor can be positioned upstream of the wound (such as at or near the inlet of the negative pressure source) and a second pressure sensor can be positioned at or near the wound or at or near a canister. This configuration can be accomplished by incorporating, in addition to one or more lumens forming a first fluid flow path connecting the negative pressure source to the wound (such as the flow path), a second fluid flow path that includes one or more lumens in which the second pressure sensor is positioned. The first and second fluid flow paths can be fluidically isolated from each other. When the at least two pressure sensors are used, the rate of change of pressure (e.g., in peak-to-peak pressure or maximum pressure) in the first and second fluid flow paths can be determined and the difference in pressure detected between the first and second pressure sensors can be determined. These values can be used separately or together to detect presence of blood in the first fluid flow path or the second fluid flow path.

For example, suppose that the first pressure sensor is positioned at or near the inlet and measures a pressure level in the canister, and the second pressure sensor is positioned at or near the wound and measures a pressure level at the wound. Further, suppose that the first pressure sensor indicates that a desired or set level of negative pressure being administered by the negative pressure source is communicated to the canister, while the second pressure sensor indicates that a lower negative pressure level (more positive pressure) is present at the wound (for instance, due to blood or blood clots being aspirated from the wound). In addition to or instead of the determined rates of change, the pressure differential between the pressure levels measured by the first and second pressure sensors can thus be used to determine and indicate presence of blood.

The level of activity of the negative pressure source, as explained herein, can be used in addition to or instead of the rate of change of pressure to determine presence of blood. When blood or blood clots enter a portion of the fluid flow path, the negative pressure source administers pressure to a smaller volume, which in turn may cause the negative pressure source to lower its activity level (e.g., to slow down a motor of the negative pressure source in the case where the negative pressure include a motor) in response to the decreased flow. This lower level of activity can be used together with or instead of determined rate of change to detect presence of blood.

In addition or alternatively to the features of the flow estimation process 10 described with respect to blocks 12, 14, 16 and as described elsewhere herein, the processor of the pump assembly 150, in some embodiments, can:

determine the estimated flow further or alternatively using a level of activity of the pump assembly 150, such as a level of activity of a source of negative pressure of the pump assembly 150; the level of activity can be determined based at least on: (i) a duty cycle of the source of negative pressure, (ii) a direct feedback measure of the level of activity of the source of negative pressure from the source of negative pressure (for example, from a signal directly output by the source of negative pressure indicative of its level of activity, such a tachometer signal or Hall effect signal from the source of negative pressure), and (iii) an indirect feedback measure of the level of activity of the source of negative pressure, such as (a) from a signal from an activity monitor (e.g., motion sensor) separate from the source of negative pressure where the signal is responsive to activity of the source of negative pressure or (b) from a signal from a pressure sensor in the TNP system 100, where the signal is responsive to activity of the source of negative pressure; for example, if the level of activity of the source of negative pressure remains substantially constant and a particular characteristic of pressure increase is detected, this can indicate decrease in the flow of the aspirated fluid, or in contrast, if the level of activity of the source of negative pressure increases (e.g., above a certain activity threshold), this can indicate presence of a blockage in the fluid flow path, not change in the flow; the level of activity of the pump assembly 150 can be determined using one or more parameters individually or in combination, such as by using a weighted average calculation;

determine flow rate directly using one or more flow sensor or flow meters (such as mass flow meters);

compare the flow rate to one or more thresholds (e.g., the one or more thresholds are selected depending on a pressure set point for the pump assembly 150) to determine whether the substance is more likely to be blood or exudate, among other possible substances, where the satisfying one or more of the thresholds indicates that the substance is more likely to be blood;

determine a confidence value associated with the estimated flow rate indicative of an estimated accuracy of the estimated flow rate relative to an actual flow rate of the substance, where the confidence value can depend at least on one or more of: (i) a mode of operation when the estimated flow rate is determined and (ii) a rate of change of pressure changes relative to one or more confidence thresholds; the confidence value can be determined, for instance, based on the rate of change of pressure and one or more of the differential pressure measurement, determination of presence of blood in the canister, or negative pressure source activity;

perform or change an operation (e.g., deactivating the source of negative pressure, entering a low power state, or activate a countdown timer for changing a setting or mode), setting (e.g., adjusting a level of activity of the source of negative pressure) of the pump assembly 150 responsive to the flow rate or the confidence value, or activating an audible or visible alarm; the alarm can be additionally or alternatively be transmitted (using wired or wireless transmission) to a remote computing device, such as a base station, remote alarm system, and the like;

actuate one or more valves positioned between a canister and the wound (such as upstream of the canister, such as between the canister and the negative pressure source) in response to detection of blood or in response to a pressure level in the fluid flow path (for instance, a valve may be opened when the level of negative pressure in the canister reaches at least −25 mmHg or another suitable value below atmospheric pressure, otherwise, the valve may be kept closed); advantageously, in certain embodiments, closing a valve between the canister and the wound can disconnect the negative pressure source from the wound in order to prevent administration of negative pressure to the wound (and causing further harm to the patient); in addition, closing the valve can prevent the canister from being available for aspirating blood; in certain implementations, the one or more valves can be opened automatically or partly by vacuum itself rather than entirely under control of the processor;

actuate one or more vents (such as using a vent valve like a solenoid valve), in response to detection of blood, to vent the fluid flow path to the atmosphere in order to prevent further administration of negative pressure to the wound; the or more vents can be positioned, for instance, (i) between the negative pressure source and the canister (to quickly depressurize the fluid flow path), (ii) between the canister and the dressing, or (iii) in another suitable position in the fluid flow path; the one or more vents can, in certain implementations, be opened immediately, soon after, or following a period of time (e.g., 0.5, 1, 2, 5, or 10 seconds) after detection of blood in the fluid flow path;

output the flow rate or the confidence value or data indicative thereof for presentation to a user, such as on a display or via an indicator like a light emitting diode (LED); or confirm presence of blood in the fluid flow path (e.g., in a canister), using one or more sensors configured to distinguish blood from exudate or tissue; for example, one of the sensors can be an optical sensor including a light source that emits light (such as visible light like red light or invisible light like infrared light) and a detector that detects changes in the properties of the light after it has passed through a substance in the fluid flow path; blood may alter light differently from exudate or tissue as it passes through, such as by absorbing energy at one or more different frequencies, which can be detected.

When negative pressure is applied to a depressurized wound (e.g., for the first time or after substantial pause in vacuum application), it may be advantageous, in certain embodiments, to determine if negative pressure is being applied too quickly so as to cause bleeding of the wound. If the wound is bleeding, it is likely that the patient is experiencing discomfort (e.g., pain) from rapid application of negative pressure. In response to detecting presence of blood in the fluid flow path, the processor can slow down the application of negative pressure so that that a negative pressure setting is reached over a longer duration of time, thereby resulting in more comfort for the patient.

In certain embodiments, a negative pressure wound therapy system can determine, based on a viscosity of a substance in a fluid flow path, the composition or properties of the substance and enable one or more appropriate actions to be taken in view of the composition or properties of the substance. For example, blood may have a higher viscosity than liquid or gaseous exudate, and thereby blood can be differentiated from exudate, among other possible substances, by determining that the composition of the aspirated substance has an estimated viscosity that satisfies one or more thresholds.

Figure 17:
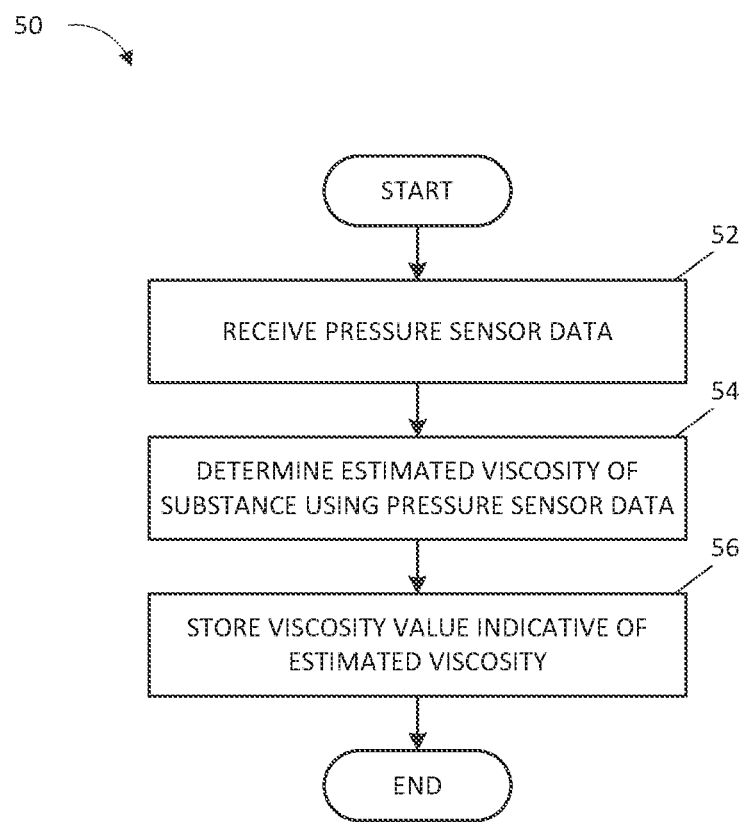
FIG. 17 illustrates a process for estimating viscosity of a fluid according to some embodiments.

FIG. 17 illustrates a viscosity estimation process 50 performable by a device, such as the pump assembly 150 of FIG. 1, the pump assembly 230 of FIG. 2, or other pump assemblies described herein. In some embodiments, the process 50 can be performed by one or more of the processors described herein. For convenience, the viscosity estimation process 50 is described in the context of the system 100 of FIG. 1, but may instead be implemented in other systems described herein or by other computing systems not shown.

The viscosity estimation process 50 can enable the pump assembly 150 to determine an estimated viscosity of a substance in the fluid flow path, which includes the tube 140, so that the pump assembly 150 can provide the estimated viscosity of the substance or differentiate between various substances (e.g., blood versus exudate) in the fluid flow path. For example, the pump assembly 150 can advantageously, in certain embodiments, output an indication of the estimated viscosity of a substance in the fluid flow path for display to a user of the pump assembly 150 or adjust an operation of the pump assembly 150, such as an operation of a source of negative pressure of the pump assembly 150 (e.g., pause operation of the source of negative pressure), in view of the estimated viscosity of the substance or a determined type of the substance in the flow fluid path.

At block 52, the process 50 can receive the pressure sensor data indicative of a measured pressure in the fluid flow path. The pressure can be measured, for instance, by one or more of the pressure sensors described herein.

At block 54, the process 50 can determine an estimated viscosity of a substance in the fluid flow path using the pressure sensor data. For example, the processor can examine a rate of change of pressure (e.g., in peak-to-peak pressure) in the fluid flow path using the pressure sensor data. The rate of change of the pressure can, for instance, be relatively higher when blood may enter or travel through the fluid flow path than when exudate enters or flows, and thus the rate of change of the pressure changes can correspond to the estimated viscosity. Because blood or tissues clots have higher viscosity than liquid exudate, the fluid flow path volume "seen" by the source of negative pressure (e.g., combined volume of the fluid flow path, which can include the tube 140, canister (if present), and wound dressing downstream of the source of negative pressure) is reduced when blood or tissue clots are aspirated into the fluid flow path. This reduction in volume can cause an increase (e.g., spike) in the sensed pressure signal. Such increase can have one or more characteristics indicative of the change in the viscosity of the aspirated material. These one or more characteristics can the identified to determine that blood or tissue clots are present in the fluid flow path.

The processor implementing the process 50 can be a processor dedicated to processing pressure sensor data from one or more of the pressure sensors and outputting one or more signals based thereon (e.g., the processor can be coupled to or mounted on the one or more pressure sensors, can be a dedicated digital signal processor (DSP), etc.), or the processor can additionally process other non-pressure sensor data and output one or more signals based thereon for the pump assembly 150.

At block 56, the process 50 can store in a memory device a viscosity value indicative of the estimated viscosity, for instance, for later reference or outputting.

In addition or alternative to the features of the viscosity estimation process 50 described with respect to blocks 52, 54, 56, the pump assembly 150, in some embodiments, can:

determine the estimated viscosity further or alternatively using a level of activity of the pump assembly 150, such as a level of activity of a source of negative pressure of the pump assembly 150; the level of activity can be determined based at least on: (i) a duty cycle of the source of negative pressure, (ii) a direct feedback measure of the level of activity of the source of negative pressure from the source of negative pressure (for example, from a signal directly output by the source of negative pressure indicative of its level of activity, such a tachometer signal or Hall effect signal from the source of negative pressure), and (iii) an indirect feedback measure of the level of activity of the source of negative pressure, such as (a) from a signal from an activity monitor (for example, motion sensor) separate from the source of negative pressure where the signal is responsive to activity of the source of negative pressure or (b) from a signal from a pressure sensor in the TNP system 100, where the signal is responsive to activity of the source of negative pressure; for example, if the level of activity of the source of negative pressure remains substantially constant and a particular characteristic of pressure increase is detected, this can indicate increase in the viscosity of the aspirated fluid, or in contrast, if the level of activity of the source of negative pressure increases (e.g., above a certain activity threshold), this can indicate presence of a blockage in the fluid flow path, not change in the viscosity; the level of activity of the pump assembly 150 can be determined using one or more parameters individually or in combination, such as by using a weighted average calculation;

determine the estimated viscosity further or alternatively using one or more other parameters such as a duration of a pressure change indicated by the pressure sensor data, blood oxygen perfusion ($SpO_2$) sensor data; the estimated viscosity can be determined using one or more of the parameters described in this disclosure individually or in combination, such as by using a weighted average calculation;

compare the viscosity value to one or more thresholds (e.g., the one or more thresholds are selected depending on a pressure set point for the pump assembly 150) to determine whether the substance is more likely to be blood or exudate, among other possible substances, where the satisfying one or more of the thresholds indicates that the substance is more likely to be blood;

determine a confidence value associated with the estimated viscosity indicative of an estimated accuracy of the estimated viscosity relative to an actual viscosity of the substance, where the confidence value can depend at least on one or more of: (i) a mode of operation when the estimated viscosity is determined and (ii) a rate of change of pressure changes relative to one or more confidence thresholds;

perform or change an operation (e.g., deactivating the source of negative pressure, entering a low power state, or activate a countdown timer for changing a setting or mode), setting (e.g., adjusting a level of activity of the source of negative pressure) of the pump assembly 150 responsive to the viscosity value or the confidence value, or activating an audible or visible alarm; or output the viscosity value or the confidence value or data indicative thereof for presentation to a user, such as on a display or via an indicator like a light emitting diode (LED).

When negative pressure is applied to a depressurized wound (e.g., for the first time or after substantial pause in vacuum application), it may be advantageous, in certain embodiments, to determine if negative pressure is being applied too quickly so as to cause bleeding of the wound. If the wound is bleeding, it is likely that the patient is experiencing discomfort (e.g., pain) from rapid application of negative pressure. In response to detecting presence of blood in the fluid flow path, the processor can slow down the negative pressure so that that a negative pressure setting is reached over a longer duration of time, thereby resulting in more comfort for the patient.

In some embodiments, an apparatus for applying negative pressure to a wound includes a negative pressure source disposed in a housing, the negative pressure source configured to be coupled, via a fluid flow path comprising at least one lumen, to a dressing configured to be placed over a wound and to provide negative pressure to the dressing. The apparatus also includes one or more pressure sensors configured to monitor a pressure in the fluid flow path and a controller configured to: while the negative pressure source provides negative pressure to the dressing, determine an estimated flow rate of a substance aspirated from the wound into the fluid flow path based at least on the pressure monitored by the one or more pressure sensors, and store, in a memory device, a flow rate value indicative of the estimated flow rate of the substance.

The apparatus of the preceding paragraph can include any one or more of the following features. The controller can be further configured to activate one of a first flow rate indicator or second flow rate indicator responsive to the flow rate value, the first flow rate indicator denoting a higher density of the substance aspirated from the wound than the second flow rate indicator. The controller can be further configured to determine the estimated flow rate of the substance based at least on one or more of (i) a rate of change of the pressure monitored by the one or more pressure sensors, (ii) a duration that the pressure monitored by the one or more pressure sensors remains at a level, (iii) a mode of operation of the controller or the negative pressure source, (iv) a level of activity of the negative pressure source, (v) a flow rate measured in the fluid flow path by a flow rate detector, (vi) a flow rate in the fluid flow path calculated by the controller, or (vii) a mass flow in the fluid flow path calculated by the controller. The controller can be further configured to determine a confidence value associated with the estimated flow rate, the confidence value being indicative of an estimated accuracy of the estimated flow rate relative to an actual flow rate of the substance. The controller can be further configured to activate one of a first confidence indicator or second confidence indicator responsive to the confidence value, the first confidence indicator denoting a higher confidence than the second confidence indicator. The controller can be further configured to modify operation of the negative pressure source responsive to at least of the flow rate value or the confidence value.

In some embodiments, an apparatus for applying negative pressure to a wound includes a negative pressure source disposed in a housing, the negative pressure source configured to be coupled, via a fluid flow path comprising at least one lumen, to a dressing placed over a wound and to provide negative pressure to the dressing. The apparatus also includes one or more pressure sensors configured to monitor a pressure in the fluid flow path and a controller configured to: while the negative pressure source provides negative pressure, detect presence of blood in the fluid flow path based at least on the pressure monitored by the one or more pressure sensors, and in response to detecting presence of blood in the fluid flow path, prevent administration of negative pressure to the wound dressing.

The apparatus of any preceding paragraph can include any one or more of the following features. The controller can be further configured to prevent administration of negative pressure to the wound dressing by at least one of: deactivating operation of the negative pressure source, opening a vent positioned in the fluid flow path, or closing a valve positioned in the fluid flow path. The controller can be further configured to detect presence of blood in a canister based at least on data from one or more optical sensors. The one or more pressure sensors can include at least two pressure sensors.

In some embodiments, an apparatus for applying negative pressure to a wound includes a negative pressure source disposed in a housing, the negative pressure source configured to be coupled, via a fluid flow path comprising at least one lumen, to a dressing configured to be placed over a wound and to provide negative pressure to the dressing. The apparatus also includes a pressure sensor configured to monitor a pressure in the fluid flow path and a controller configured to while the negative pressure source provides negative pressure to the dressing, determine an estimated viscosity of a substance aspirated from the wound into the fluid flow path based at least on the pressure monitored by the pressure sensor, and store, in a memory device, a viscosity value indicative of the estimated viscosity of the substance.

The apparatus of any preceding paragraph can include any one or more of the following features. The controller can be further configured to activate one of a first viscosity indicator or second viscosity indicator responsive to the viscosity value, the first viscosity indicator denoting a higher viscosity than the second viscosity indicator. The controller can be configured to determine the estimated viscosity of the substance further based at least on one or more of (i) a rate of change of the pressure monitored by the pressure sensor, (ii) a duration that the pressure monitored by the pressure sensor remains at a level, (iii) a mode of operation of the controller or the negative pressure source, or (iv) a level of activity of the negative pressure source. The controller can be further configured to determine a confidence value associated with the estimated viscosity, the confidence value being indicative of an estimated accuracy of the estimated viscosity relative to an actual viscosity of the substance. The controller can be further configured to activate one of a first confidence indicator or second confidence indicator responsive to the confidence value, the first confidence indicator denoting a higher confidence than the second confidence indicator. The controller can be further configured to modify operation of the negative pressure source responsive to at least of the viscosity value or the confidence value.

Some embodiments relate to a method of operating, using, or manufacturing the apparatus of any preceding paragraph.

Terminology

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The invention claimed is:

1. An apparatus for applying negative pressure to a wound, comprising:
   a negative pressure source configured to provide negative pressure, via a fluid flow path, to a dressing placed over a wound;
   one or more pressure sensors configured to monitor a pressure in the fluid flow path; and
   a controller programmed to:
      determine a viscosity of a fluid in the fluid flow path based on a change of the pressure monitored by the one or more pressure sensors over a time duration, wherein the change of the pressure monitored over the time duration indicates an increase in pressure resulting from flow of a first fluid having a higher viscosity than a second fluid;
      detect presence of blood in the fluid flow path based on the viscosity of the fluid, the pressure monitored by the one or more pressure sensors, and an activity level of the negative pressure source, and
      provide an indication that blood is present in the fluid flow path, wherein the indication comprises decreasing a target negative pressure provided by the negative pressure source or deactivating the negative pressure source.

2. The apparatus of claim 1, wherein the negative pressure source comprises a pump operated by an actuator, and wherein the activity level comprises at least one of a pump speed, a pulse width modulation (PWM) signal configured to drive the actuator, or a current signal configured to drive the actuator.

3. The apparatus of claim 1, wherein the controller is further programmed to:
   compute a first indicator associated with change in the pressure over a time duration and a second indicator associated with change in the activity level over the time duration; and
   detect presence of blood based on the first and second indicators.

4. The apparatus of claim 3, wherein at least one of the first or second indicators comprises a statistical indicator.

5. The apparatus of claim 3, wherein the controller is further programmed to: perform a time series analysis to determine if at least one of the first or second indicators deviates from a threshold, and based on the determination of deviation, detect presence of blood.

6. The apparatus of claim 5, wherein the time series analysis comprises determination of a cumulative sum (Cusum) of at least one of the first or second indicators.

7. The apparatus of claim 6, wherein the Cusum of at least one of the first or second indicators comprises a sliding causal Cusum.

8. The apparatus of claim 3, wherein the first indicator comprises mean pressure over the time duration and the second indicator comprises standard deviation of standard deviation of a current signal over the time duration, the current signal configured to drive the negative pressure source.

9. The apparatus of claim 1, wherein the indication that blood is present in the fluid flow path further comprises one or more of: activation of an alarm or release of negative pressure in the fluid flow path.

10. The apparatus of claim 1, wherein the controller is further programmed to detect and provide indication of one or more of: presence of water in the fluid flow path, presence of exudate in the fluid flow path, presence of gas leak in the fluid flow path, or change in the pressure in the fluid flow path.

11. The apparatus of claim 10, wherein the controller is further programmed to:
compute a plurality of indicators associated with change in the pressure over a time duration and change in the activity level over the time duration; and
detect and provide an indication of one or more of presence of water in the fluid flow path, presence of exudate in the fluid flow path, presence of gas leak in the fluid flow path, or change in the pressure in the fluid flow path based on the plurality of indicators.

12. The apparatus of claim 11, wherein at least some of the plurality of indicators comprise a statistical indicator.

13. The apparatus of claim 11, wherein the controller is further programmed to: perform a time series analysis to determine if at least some of the plurality of indicators deviate from one or more thresholds, and based on the determination of deviation, detect one or more of presence of water in the fluid flow path, presence of exudate in the fluid flow path, presence of gas leak in the fluid flow path, or change in negative pressure in the fluid flow path.

14. The apparatus of claim 13, wherein the time series analysis comprises determination of a cumulative sum (Cusum) of at least some of the plurality of indicators.

15. The apparatus of claim 14, wherein the Cusum of at least some of the plurality of indicators comprises a sliding causal Cusum.

16. The apparatus of claim 11, wherein the negative pressure source comprises a pump operated by an actuator, and wherein an indicator associated with change in the pressure in the fluid flow path comprises mean pressure over the time duration, an indicator associated with presence of gas leak in the fluid flow path comprises standard deviation of a mean of a current signal configured to drive the actuator, and an indicator associated with presence of water or exudate in the fluid flow path comprises kurtosis of standard deviation of a pump speed.

17. The apparatus of claim 11, wherein the controller is further programmed to determine malfunction of the one or more pressure sensors based on at least one of the plurality of indicators.

18. The apparatus of claim 1, wherein the change of the pressure comprises a change of a peak-to-peak measurement of the pressure monitored over the time duration.

19. The apparatus of claim 1, wherein the one or more pressure sensors comprises a single pressure sensor.

* * * * *